(12) United States Patent
Ouyang et al.

(10) Patent No.: US 9,895,048 B2
(45) Date of Patent: Feb. 20, 2018

(54) HANDHELD ENDOSCOPE

(71) Applicant: UroSee Corporation, Bellevue, WA (US)

(72) Inventors: Xiaolong Ouyang, Bellevue, WA (US); Chih-Yu Ting, New Taipei (TW); Shih-Ping Wang, Palo Alto, CA (US)

(73) Assignee: UROSEE CORP., Bellevue, WA (US)

( * ) Notice: Subject to any disclaimer, the term of this patent is extended or adjusted under 35 U.S.C. 154(b) by 0 days.

(21) Appl. No.: 15/371,858

(22) Filed: Dec. 7, 2016

(65) Prior Publication Data

US 2017/0188795 A1 Jul. 6, 2017

Related U.S. Application Data

(63) Continuation-in-part of application No. PCT/US2016/018670, filed on Feb. 19, 2016, and a
(Continued)

(51) Int. Cl.
*A61B 1/015* (2006.01)
*A61B 1/307* (2006.01)
(Continued)

(52) U.S. Cl.
CPC ...... *A61B 1/00105* (2013.01); *A61B 1/00066* (2013.01); *A61B 1/00119* (2013.01);
(Continued)

(58) Field of Classification Search
CPC ............ A61B 1/00105; A61B 1/00066; A61B 1/00121; A61B 1/00124; A61B 1/00128;
(Continued)

(56) References Cited

U.S. PATENT DOCUMENTS 5,188,093 A * 2/1993 Lafferty ............. A61B 1/00096
600/109
5,486,155 A * 1/1996 Muller ............... A61B 1/00135
600/105
(Continued)

FOREIGN PATENT DOCUMENTS

| WO | WO2012060932 | 5/2012 |
| WO | WO2014031192 | 2/2014 |
| WO | WO2014/065901 | 5/2014 |

OTHER PUBLICATIONS

Jul. 12, 2016 International Search Report and Written Opinion in connection with corresponding International Application No. PCT/US2016/18670.

*Primary Examiner* — John P Leubecker
(74) *Attorney, Agent, or Firm* — Cooper & Dunham LLP

(57) ABSTRACT

A handheld endoscope has a disposable, single-use portion that includes a fluid hub, cannula and distal tip and a re-usable portion that includes a handle and display module. The electrical connection between the single-use and reusable portions is distally spaced from their mechanical connection and from the fluid hub. The distal tip includes LED illumination and an imaging module that feeds live video to the display module that is rotatable to allow viewing by the operator and others. The cannula and fluid hub are rotatable relative to the handle and includes separate lumens for fluid flow and an electrical cable. The fit resists rotation to maintain the relative positions of the cannula and handle until the application of a torque threshold. The single-use and re-usable portions mate and un-mate with each other via the physically separated mechanical and electrical connectors. Extruded cannula and molded distal tip parts can be separately formed which aids in manufacturing and assembly.

31 Claims, 19 Drawing Sheets

Related U.S. Application Data continuation-in-part of application No. 14/913,867, filed on Feb. 23, 2016.

(60) Provisional application No. 62/275,222, filed on Jan. 5, 2016, provisional application No. 62/275,241, filed on Jan. 6, 2016, provisional application No. 62/279,784, filed on Jan. 17, 2016, provisional application No. 62/287,901, filed on Jan. 28, 2016, provisional application No. 62/299,453, filed on Feb. 24, 2016, provisional application No. 62/339,810, filed on May 21, 2016, provisional application No. 62/362,643, filed on Jul. 15, 2016, provisional application No. 62/375,814, filed on Aug. 16, 2016, provisional application No. 62/405,930, filed on Oct. 9, 2016, provisional application No. 62/416,403, filed on Nov. 2, 2016.

(51) Int. Cl.
*A61B 1/05* (2006.01)
*A61B 1/00* (2006.01)
*A61B 1/04* (2006.01)
*A61B 1/06* (2006.01)

(52) U.S. Cl.
CPC ...... *A61B 1/00124* (2013.01); *A61B 1/00128* (2013.01); *A61B 1/00135* (2013.01); *A61B 1/015* (2013.01); *A61B 1/04* (2013.01); *A61B 1/0684* (2013.01); *A61B 1/307* (2013.01); *A61B 1/00103* (2013.01); *A61B 1/00108* (2013.01)

(58) Field of Classification Search
CPC ......... A61B 1/05; A61B 1/0684; A61B 1/307; A61B 1/303; A61B 1/015; A61B 1/00103; A61B 1/00108
See application file for complete search history.

(56) References Cited

U.S. PATENT DOCUMENTS

| | | | |
|---|---|---|---|
| 5,860,953 A * | 1/1999 | Snoke | A61B 1/00105 |
| | | | 604/95.04 |
| 5,928,137 A | 7/1999 | Green | |
| 5,935,141 A | 10/1999 | Weldon | |
| 7,798,995 B2 | 9/2010 | Yue | |
| 8,187,171 B2 * | 5/2012 | Irion | A61B 1/05 |
| | | | 600/110 |
| 8,696,552 B2 * | 4/2014 | Whitman | A61B 1/00135 |
| | | | 600/133 |
| 2005/0085695 A1 | 4/2005 | Shener et al. | |
| 2006/0114986 A1 * | 6/2006 | Knapp, II | A61B 1/00103 |
| | | | 375/240.01 |
| 2006/0173245 A1 | 8/2006 | Todd et al. | |
| 2007/0162095 A1 * | 7/2007 | Kimmel | A61B 1/00089 |
| | | | 600/109 |
| 2008/0108869 A1 * | 5/2008 | Sanders | A61B 1/00105 |
| | | | 600/109 |
| 2011/0009694 A1 | 1/2011 | Schultz et al. | |
| 2012/0100729 A1 * | 4/2012 | Edidin | H01R 13/6205 |
| | | | 439/38 |
| 2012/0289858 A1 | 11/2012 | Ouyang et al. | |
| 2013/0150672 A1 * | 6/2013 | Fujitani | G02B 23/2476 |
| | | | 600/137 |
| 2013/0035553 A1 | 7/2013 | Konstorum | |
| 2013/0345514 A1 | 12/2013 | Manion | |
| 2014/0107416 A1 * | 4/2014 | Birnkrant | A61B 1/00016 |
| | | | 600/110 |
| 2014/0180007 A1 * | 6/2014 | Edidin | A61B 1/05 |
| | | | 600/122 |
| 2015/0018622 A1 | 1/2015 | Tesar et al. | |
| 2015/0150441 A1 * | 6/2015 | Ouyang | A61B 1/307 |
| | | | 600/109 |
| 2015/0164313 A1 * | 6/2015 | Ouyang | A61B 1/00103 |
| | | | 600/103 |
| 2016/0174819 A1 * | 6/2016 | Ouyang | A61B 1/00103 |
| | | | 600/105 |
| 2016/0334694 A1 * | 11/2016 | Liu | H04N 5/23209 |
| 2017/0086651 A1 * | 3/2017 | Sato | A61B 1/0052 |
| 2017/0295347 A1 * | 10/2017 | Schneider | H04N 7/185 |
| 2017/0310858 A1 * | 10/2017 | Mueckl | A61B 1/0057 |

* cited by examiner

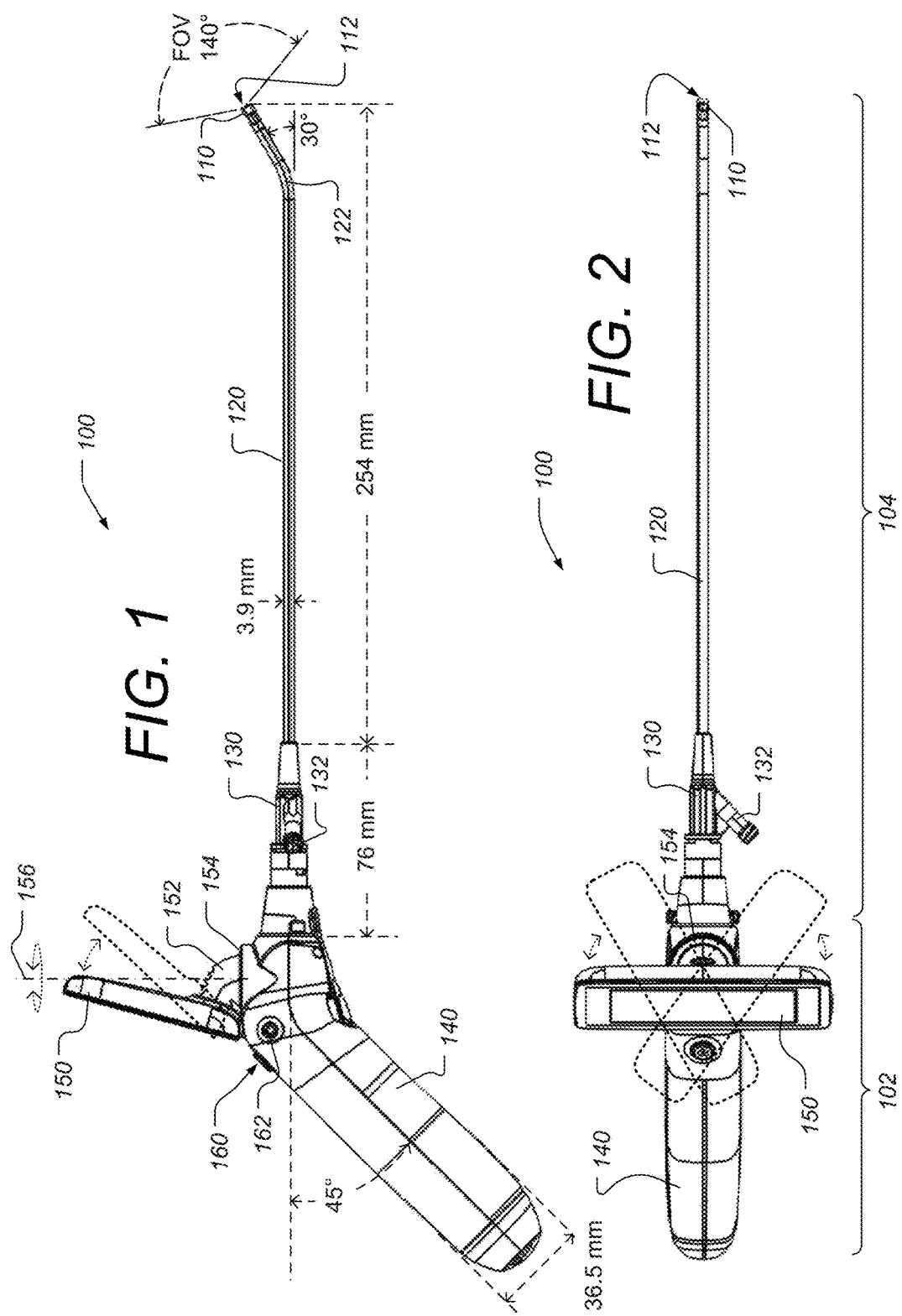

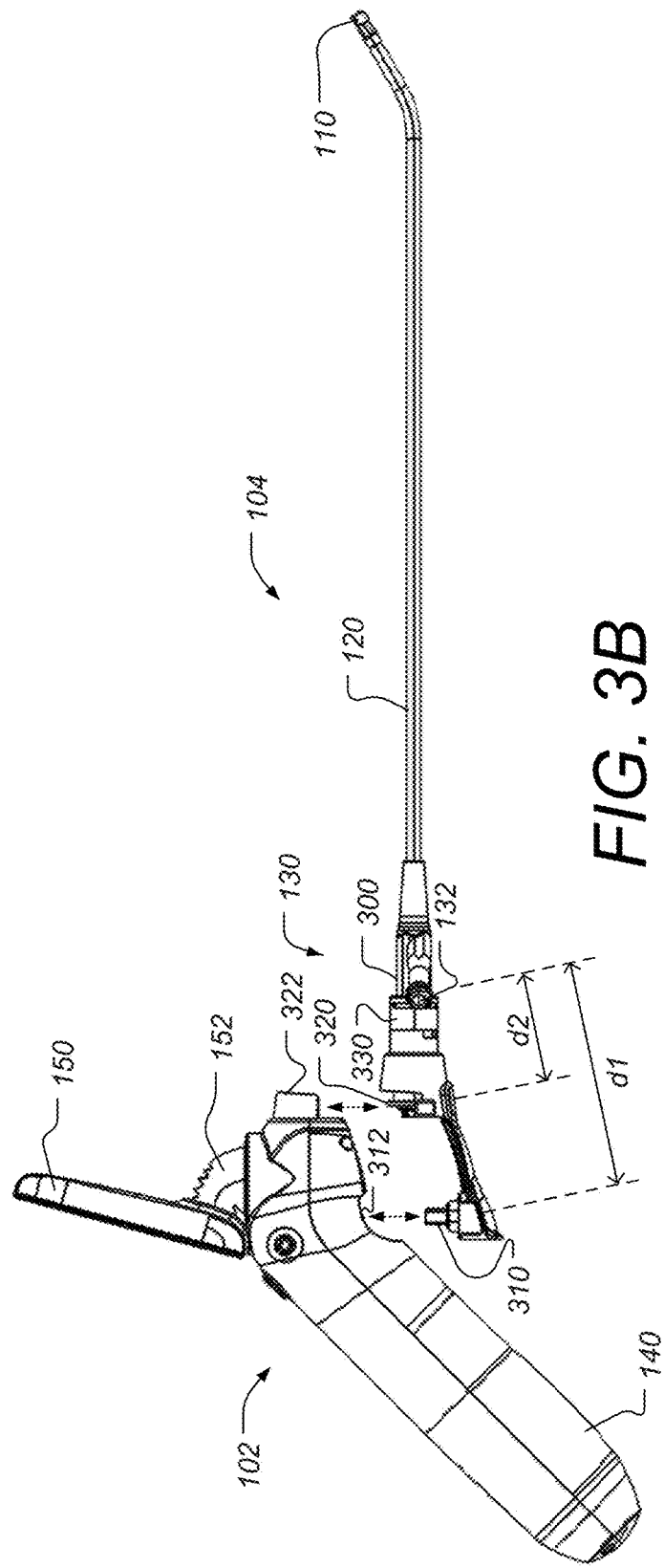

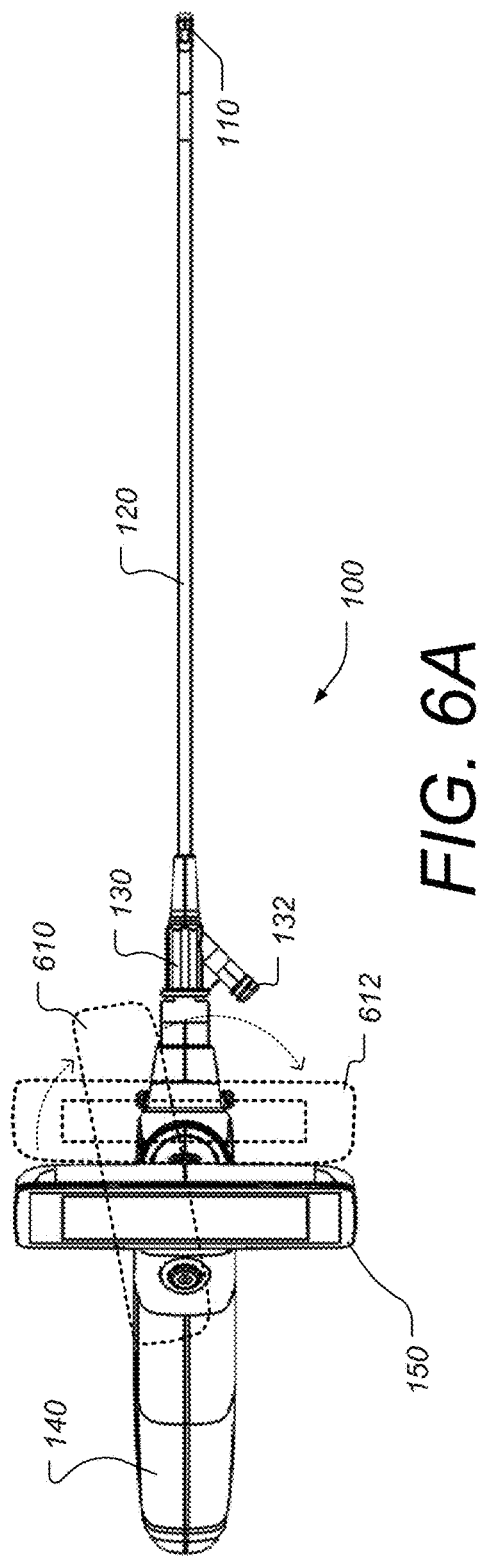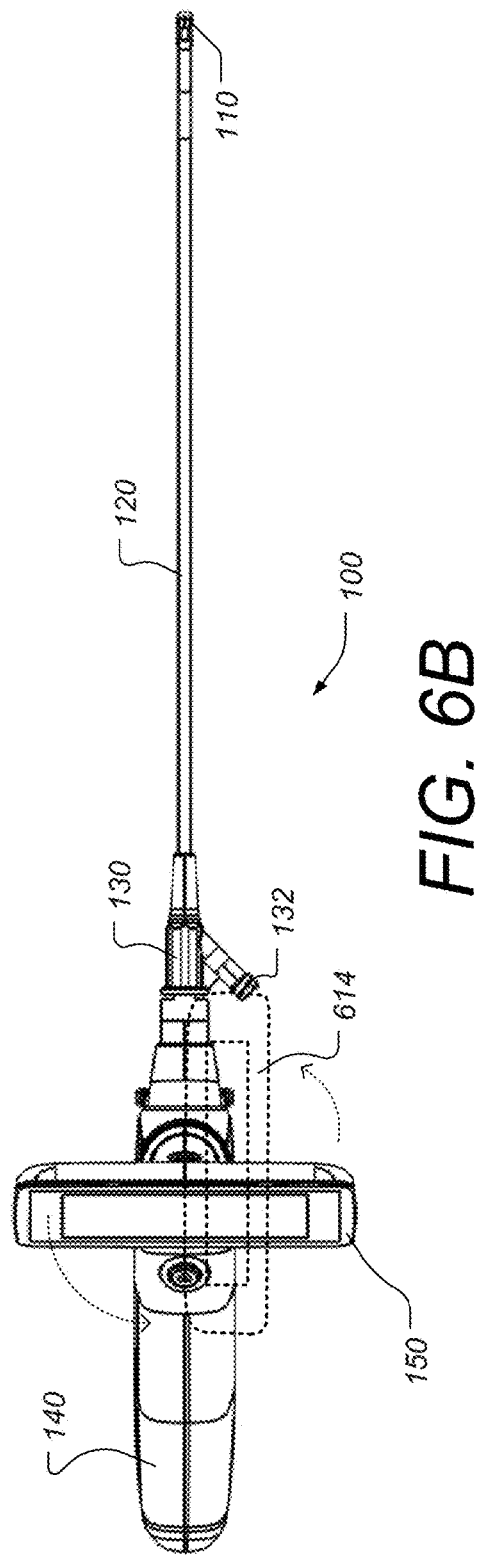

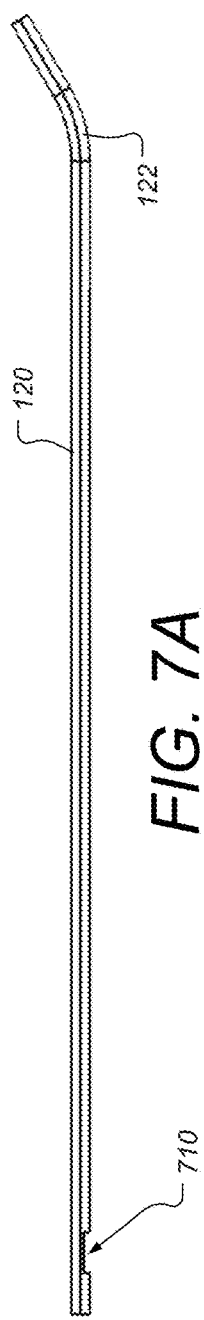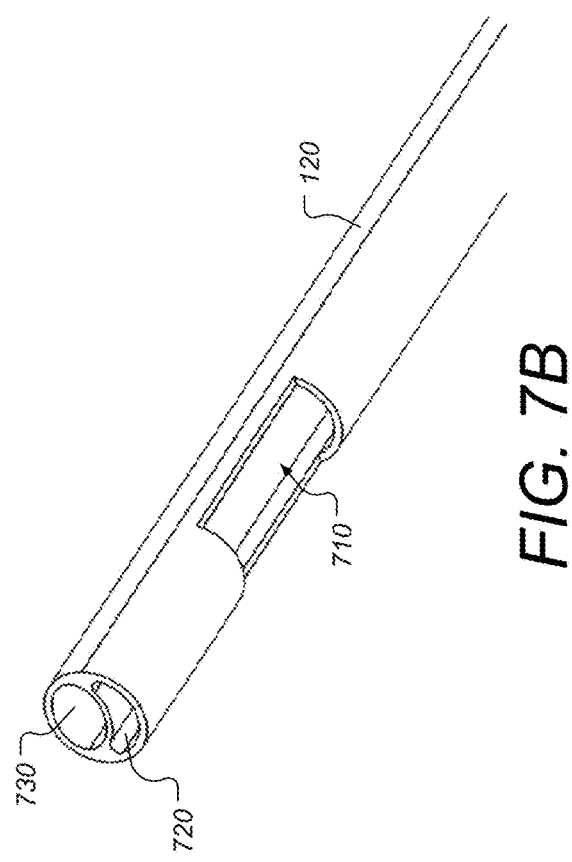

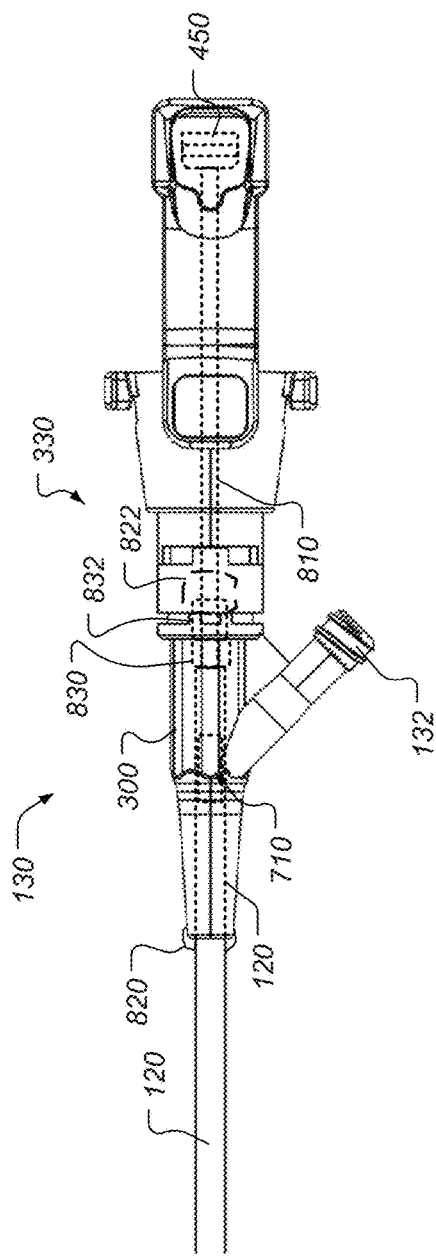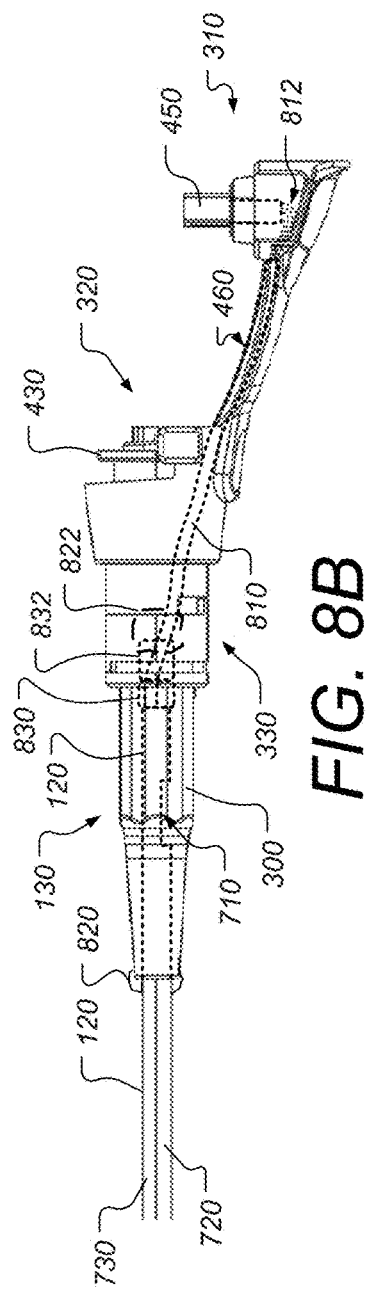
FIG. 8A
FIG. 8B

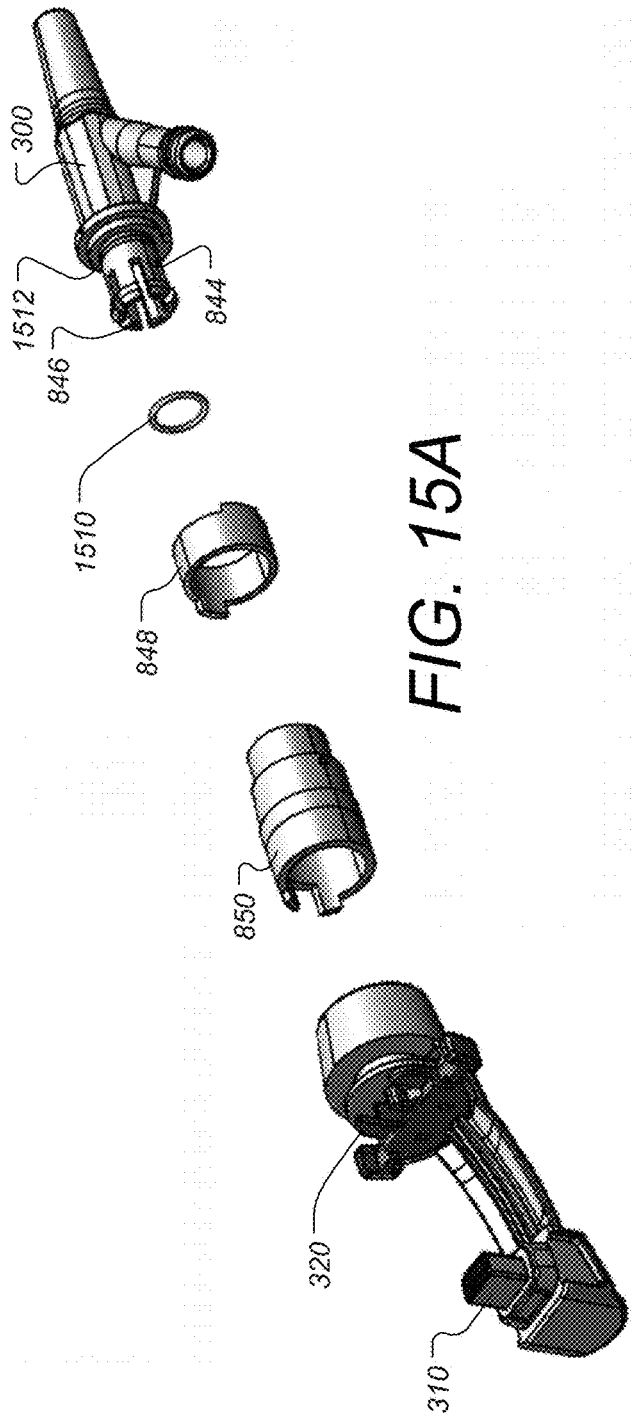
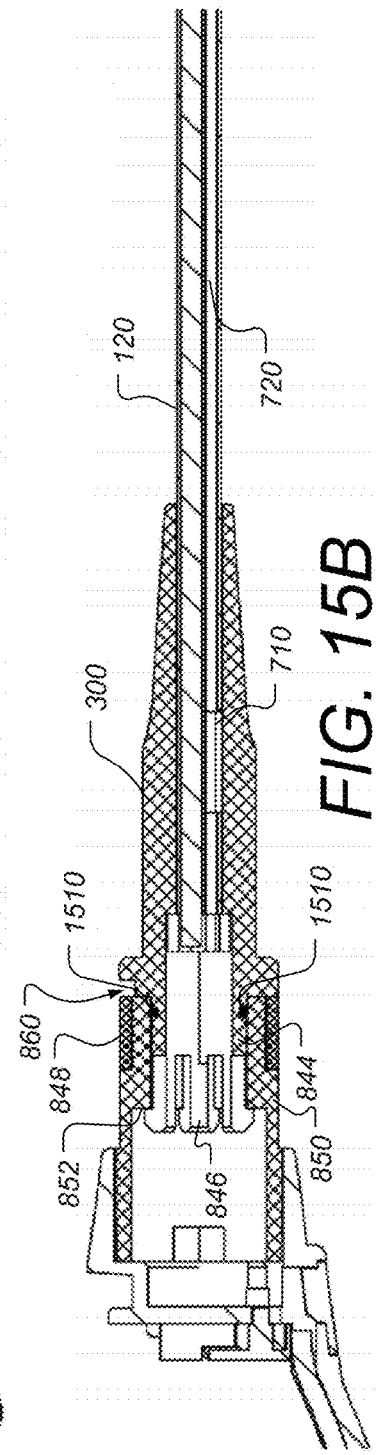

HANDHELD ENDOSCOPE

REFERENCE TO RELATED APPLICATIONS

This patent application claims the benefit of and incorporates by reference each of the following provisional applications:
U.S. Prov. Ser. No. 62/275,222 filed Jan. 5, 2016;
U.S. Prov. Ser. No. 62/275,241 filed Jan. 6, 2016;
U.S. Prov. Ser. No. 62/279,784 filed Jan. 17, 2016;
U.S. Prov. Ser. No. 62/287,901 filed Jan. 28, 2016;
U.S. Prov. Ser. No. 62/299,453 filed Feb. 24, 2016;
U.S. Prov. Ser. No. 62/339,810 filed May 21, 2016;
U.S. Prov. Ser. No. 62/362,643 filed Jul. 15, 2016;
U.S. Prov. Ser. No. 62/375,814 filed Aug. 16, 2016;
U.S. Prov. Ser. No. 62/405,930 filed Oct. 9, 2016; and
U.S. Prov. Ser. No. 62/416,403 filed Nov. 2, 2016.
This patent application is a continuation-in-part of and incorporates by reference each of the following applications:
U.S. Ser. No. 14/913,867 filed Feb. 23, 2016; and
International Patent Application No. PCT/US16/18670 filed Feb. 19, 2016.
This patent application relates to the following provisional and non-provisional applications that are each incorporated by reference:
U.S. Prov. Ser. No. 62/119,521 filed Feb. 23, 2015;
U.S. Prov. Ser. No. 62/120,316 filed Feb. 24, 2015;
U.S. Prov. Ser. No. 62/139,754 filed Mar. 29, 2015; and
U.S. Prov. Ser. No. 62/254,718 filed Nov. 13, 2015.
U.S. Prov. Ser. No. 62/259,991 filed Nov. 25, 2015;

FIELD

This patent specification generally relates mainly to a medical device for use in tissue examinations such as in urology or endoscopic surgery. More particularly, some embodiments relate to an integrated, handheld, low-cost medical device having a single-use portion and a multiple-use portion.

BACKGROUND

Conventional endoscopy, or direct vision used to examine the interior of a hollow organ or cavity of the body, uses a complex lens system for transmitting the image for the distal tip of the endoscope to a viewer. The lens system is typically a relay lens system in the case of rigid endoscopes or a bundle of fiber optics or an objective lens system in the case of flexible endoscopes. In the case of both rigid and flexible conventional endoscopes, the lens or fiber optic system is relatively expensive and is intended to be re-used many times. Therefore, stringent decontamination and disinfection procedures need to be carried out after each use.

Disposable endoscopy is an emerging category of endoscopic instruments. In some cases the manufacture of endoscopes can be made inexpensive enough to be used on a single patient only. Disposable or single-use endoscopy lessens the risk of cross-contamination and hospital acquired diseases. Partially disposable endoscopy systems for hysteroscopy are discussed in U.S. Pat. No. 8,460,182, incorporated by reference herein. A hysteroscope having a disposable probe was offered by Endosee Corporation of Los Altos, Calif., and is now offered by CooperSurgical, Inc. of Trumbull, Conn., a company that acquired EndoSee Corporation.

The subject matter described or claimed in this patent specification is not limited to embodiments that solve any specific disadvantages or that operate only in environments such as those described above. Rather, the above background is only provided to illustrate one exemplary technology area where some embodiments described herein may be practiced.

SUMMARY

According to some embodiments that are particularly suitable for fields such as urology and endoscopic surgery rather than hysteroscopy, a low-cost medical instrument for examining a patients tissue comprises a hand-held endoscope that has a single-use portion and a reusable portion. The single-use portion includes a fluid hub and connector assembly comprising a mechanical connector, an electrical connector, and a fluid hub with a fluid port, wherein the mechanical connector is at an intermediate region of the assembly and is spaced a selected distance proximally from the fluid hub, and the electrical connector is at a proximal region of the assembly and is spaced proximally from the fluid hub by a distance greater than said selected distance, and a cannula secured to a distal region of the fluid hub and comprising (i) a video camera and a light source at a distal region thereof, (ii) a fluid port at a proximal region thereof in fluid flow communication with the fluid hub's fluid port and a fluid port at the cannula's distal region, (iii) a fluid flow lumen between the cannula's fluid ports, (iv) an electrical cable lumen separate from the fluid flow lumen and extending between the cannula's distal and proximal regions, and (v) a splice-free cable extending from the video camera and light source to the electrical connector that is proximally spaced from the mechanical connector. The reusable portion comprises a handle configured to be grasped by a user's hand, a video screen mounted on the handle and configured for rotational motion around two axes that are transverse to each other and to a long axis of the cannula, to different orientations relative to the handle, a mechanical connector at a distal portion of the handle, configured to mate with the mechanical connector of the fluid hub and connector assembly to lock and unlock by hand the handle and the single-use portion to and from each other, an electrical connector spaced proximally from the mechanical connector on the handle and configured to connect to and disconnect electrically the handle to and from the fluid hub and connector assembly by hand. The fluid hub and connector assembly further comprises an outer sleeve integral with or affixed to the assembly's mechanical connector, wherein a proximal portion of the fluid hub is mounted to the outer sleeve for rotation together with the cannula relative to the assembly's mechanical connector, and a rotation limiter comprising a first slot at one of said outer sleeve and fluid hub and a first tab at the other, said first slot having stops to limit the angular extend of the first tab's travel in the first slot to limit the angular extent of rotation between (i) the outer sleeve and the assembly's mechanical connector and (ii) the fluid hub and cannula. The fluid hub is mounted to the outer sleeve in a fit configured to maintain the relative rotational positions of the handle and cannula until a torque threshold is met. The torque threshold can be in the 0.04-0.2 newton meters (N·m) range, preferably equals or exceeds 0.07 N·m, and most preferably is about 0.1 N·m. The fluid hub can be mounted to the outer sleeve in a frictional fit.

The fluid hub can be sealed against proximal fluid flow at a location distal from the mechanical connector of the single-use portion, and the electrical cable can extend splice-free proximally from the location where the fluid hub is sealed to the location of the electrical connector of the single-use portion of the endoscope.

The rotation limiter further can be in the form of a ring mounted for limited angle of rotation relative to both the outer ring and the fluid hub, wherein the first slot and first tab are at the ring and the fluid hub, and the ring and the outer sleeve comprise a second slot and a second tab that rides in the second slot and engages ends thereof to limit relative rotation between the ring and outer sleeve, wherein the first and second slots and ends thereof are positioned to permit greater angle of rotation of the cannula relative to the outer ring and thus the handle that either of the slots alone.

The endoscope can further include an angle encoder configured to detect degree of a rotation of the cannula relative to the handle, and an electronic facility operatively connected to the angle encoder and to the video screen and configured to rotate an image on the screen in relation to rotation of the cannula relative to the handle. The video screen can be offset from a long axis of the cannula to rotate relative to the handle to positions including a position in which the screen faces the cannula's distal region to thereby facilitate visualization by a patient undergoing a procedure with the endoscope. The cannula's distal region can be a molded housing for the video camera and light source while the cannula's more proximal regions can be extruded. The cannula's distal region and at least an intermediate region of the cannula an include a hydrophilic coating. The light source at the cannula's distal region can comprise four or more LEDs recessed proximally from a front surface of the cannula's distal region, and a peripheral portion of a distal end of the cannula's distal region can be rounded to facilitate insertion of the cannula in a patient's passage and movement of the cannula along the passage.

In one embodiment, an endoscope comprises a reusable portion having a handle with a mechanical connector at a distal region, an electrical connector at an intermediate region, and a video screen mounted on the handle, and further comprises a single-use portion having: a cannula with a video camera, a light source and a fluid port at a distal region, a fluid port at a proximal region, and a fluid lumen connecting the fluid ports and configured for fluid flow between the cannula's ports; a fluid hub having a distal region secured to the proximal region of the cannula and a fluid port communicating with the fluid port at the cannula's proximal region for fluid flow; an outer sleeve having a distal region to which a proximal portion of the fluid hub is rotatably mounted and further having a proximal region forming a mechanical connector releasably interlocking by hand with the reusable portion's mechanical connector to thereby interlock the single-use and reusable portions into said endoscope; a slot- and tab mechanism at said outer sleeve and fluid hub configured to limit the angle of rotation between the outer sleeve and the fluid hub; a cable extending splice-free from the distal to the proximal regions of the cannula, and thence through at least a part of the fluid hub and the outer ring and to the single-use portion's electrical connector; and a seal at a proximal portion of the fluid hub configured to keep fluid from the fluid lumen and the fluid port of the fluid hub from moving in the proximal direction from the seal, thereby keeping the mechanical connectors of both the single-use and reusable portions and the electrical connectors of both the single-use and the reusable portions free of such fluid. The video screen can be mounted to the handle for rotation between a proximally facing position and a distally facing position, and can be offset from a long axis of the cannula. The endoscope can further include a positional sensor configured to detect rotation between the handle and cannula, and a circuit coupled with the positional sensor and configured to rotate an image on the screen as a function of rotation detected by the position sensor.

The cannula's distal region can comprise a housing for said video camera and light source at a tip of the cannula and a metal sleeve affixing the housing to the remainder of the cannula. The handle can comprise a pistol grip angled relative to a long axis of the cannula, and buttons controlling the video camera and light source at an upper region of the pistol grip. The light source can comprise plural, for example at least four, LEDs circumferentially arranged around an outer periphery of the video camera and recessed from a front face of a distal end of the cannula, said distal end of the camera having a rounded periphery facilitating insertion and movement of the cannula.

The mounting of the fluid hub to the outer sleeve can be configured to resist rotation between the cannula and the handle and maintain their relative positions until torque meeting a threshold condition is applied.

One embodiment of a hand-held endoscope comprises a single-use portion having a proximal housing, a mechanical connector integral with or affixed to the proximal housing, an electrical connector proximally spaced from the mechanical connector, a fluid hub that is rotatably mounted to the proximal housing and has a fluid port and is sealed against proximal fluid flow at a location distal from said mechanical connector, and a cannula extending distally from a distal portion of the fluid hub and having (i) a proximal port configured for fluid flow communication with the fluid hub's port, a distal fluid port, and a fluid lumen connecting the cannula's ports; and (ii) a video camera and a light source at a distal region. The reusable portion comprises a handle, a video screen mounted thereon for rotation relative to the handle, a mechanical connector that is at a distal region of the handle and releasably mates and interlocks by hand with the single-use portion's mechanical connector and thus with the single-use portion, and an electrical connector that is proximally spaced from the mechanical connector and releasably maties by hand with the single-use portion's electrical connector to establish an electrical connection between the single-use and releasable portions. The fluid hub comprises a seal against fluid flow proximally from the fluid hub and into the proximal housing, and the single-use portion further comprises a splice-free cable extending from the video camera and light source to the single-use portion's electrical connector.

The rotatable mount of the fluid hub to the proximal housing can be configured to resist rotation and maintain the relative positions of the fluid hub and proximal housing until the application of torque exceeding 0.04 N·m.

The video screen can be mounted for rotation between facing proximally and facing distally.

The single-use portion's electrical connector can extend proximally from the single-use portion's mechanical connector by a distance greater than the distance between the fluid hub and the handle, thereby facilitating protection of the electrical connectors of both the reusable portion and the single-use portion from fluid in the cannula and fluid hub.

The handle's mechanical connector can comprise a semi-circular slot and distal projections surrounded by the slot, and the single-use portion's mechanical connector can comprise a plate shaped and dimensioned to be snugly received in the semicircular slot and having flexible hooked tabs configured to engage the handle's tabs and secure the single-use and reusable portions to each other, and a pair of buttons connected to the flexible tabs and extending outside the circular plate, operative to press the flexible tabs by hand out of engagement with the handle's tabs to thereby allow the plate to slide out of the handle and thus permit removal of the single-use portion from the reusable portion.

On one embodiment, an endoscopy method comprises providing a reusable portion with a mechanical connector at a distal region, an electrical connector at an intermediate region, and a video screen, and further providing a single-use portion in sterile packaging that has an assembled set of (i) a cannula with a video camera, a light source, and a fluid port at a distal region, a fluid port at a proximal region, a fluid lumen between the fluid ports, and a cable lumen from the camera and light source to the distal region of the cannula, (ii) a fluid hub having a distal region secured to the proximal region of the cannula and a fluid port at an intermediate region in fluid flow communication with the port at the cannula's proximal region, (iii) a coupler that has a mechanical connector at an intermediate region, a distal region rotatably coupled with a proximal region of the fluid hub, and an electrical connector at a region that extends proximally of the mechanical connector by at least the distance between the mechanical connector and the fluid hub. The method further comprises unpacking the single-use portion and releasably (i) interlocking the mechanical connector of the coupler to the mechanical connector of the reusable portion by hand, and (ii) the electrical connector of the unpacked portion to the electrical connector of the reusable portion, thereby releasably assembling an endoscope in which the electrical connection of the single-use to the reusable portion is separate and spaced proximally from the mechanical connection that interlocks the single-use and reusable portions to each other and, after a patient procedure, removing the single-use portion from the reusable portion by hand-action on a release mechanism formed by portions of the single-use portion and the reusable portion. The method can further comprise configuring the rotatable connection between the coupler and the fluid hub to resist rotation until torqued to a threshold of at least 0.04 N·m The method can further include inserting a guide wire through the fluid hubs fluid port and into and through the cannula's fluid lumen and out of the cannula's distant fluid port. The method can still further include providing a splice-free electrical cable extending from the video camera and light source to the single-use portion's electrical connector, and rotating the video screen between a proximally facing position and a distally facing position. As used herein, the grammatical conjunctions "and", "or" and "and/or" are all intended to indicate that one or more of the cases, object or subjects they connect may occur or be present. In this way, as used herein the term "or" in all cases indicates an "inclusive or" meaning rather than an "exclusive or" meaning. If used herein the terms "surgical" or "surgery" refer to any physical intervention on a patient's tissues, and does not necessarily involve cutting a patient's tissues or closure of a previously sustained wound.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments and are therefore not to be considered limiting of the scope of this patent specification or the appended claims. The subject matter hereof will be described and explained with additional specificity and detail through the use of the accompanying drawings in which:

FIGS. 1 and 2 are a right side view and a top view, respectively, of a handheld endoscope, according to some embodiments;

FIGS. 3A and 3B are perspective and side views showing aspects of attachment and detachment of single-use and reusable portions of a handheld endoscope, according to some embodiments;

FIGS. 6A and 6B are top views illustrating further aspects of the rotatable display module on a handheld endoscope, according to some embodiments;

FIGS. 7A and 7B are a side view and perspective views of a cannula used on a handheld endoscope, according to some embodiments;

FIGS. 8A, 8B and 8C are top, side and perspective views illustrating further aspects of the fluid hub uses on a handheld endoscope, according to some embodiments;

FIGS. 15A and 15B are perspective and cross-sectional views of a single-use portion of a handheld endoscope, according to some embodiments.

DETAILED DESCRIPTION

Figure 3A:
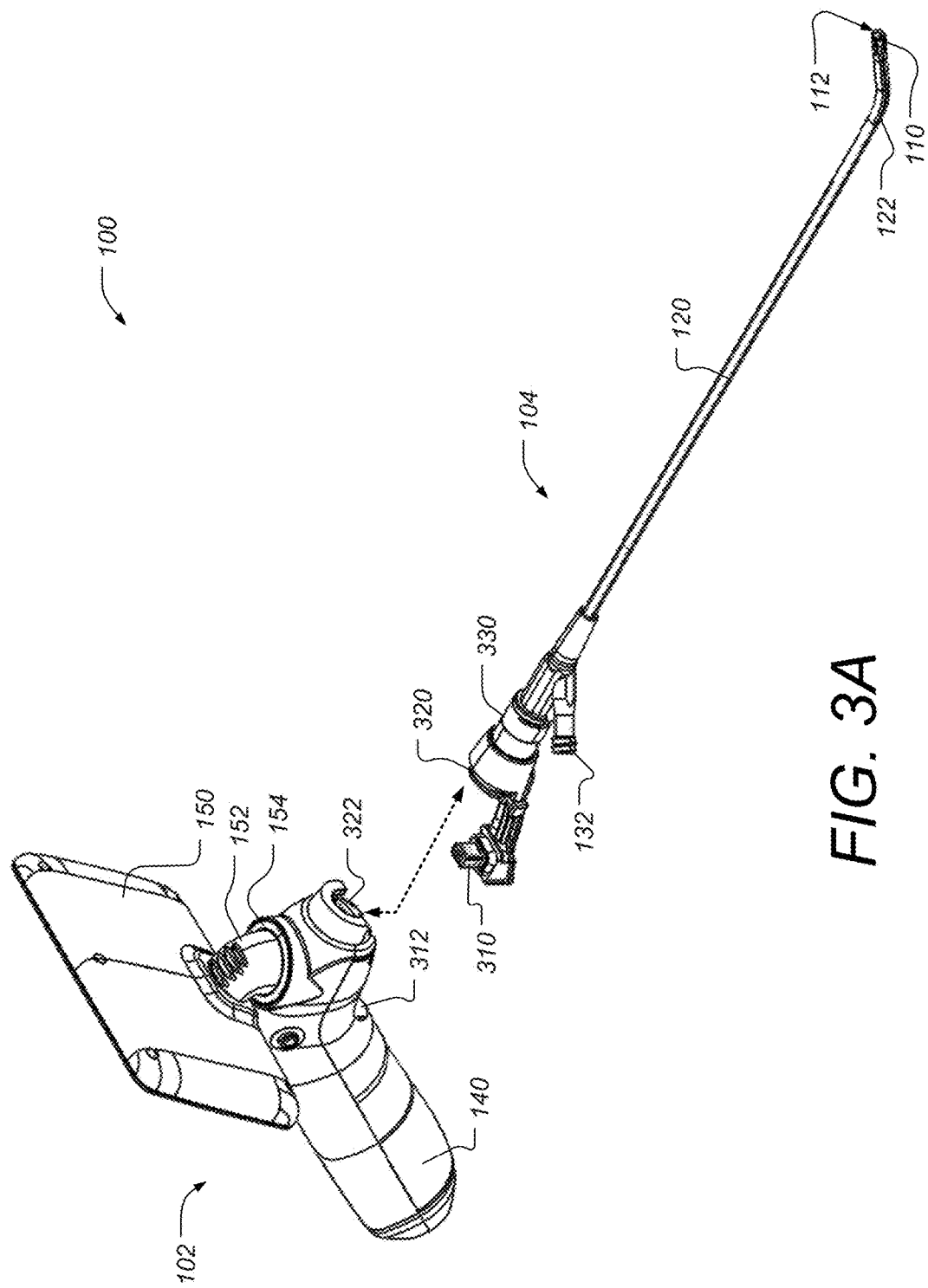

A detailed description of examples of preferred embodiments is provided below. While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

FIGS. 1 and 2 are a right side view and a top view, respectively, of a handheld endoscope, according to some embodiments. The endoscope 100 includes an elongated cannula 120 with a distal tip 112 for inserting into a hollow organ or cavity of the body. According to some embodiments, a separate tip sub-assembly 110 is attached to the cannula 120 which can be made from an extruded material. Sub-assembly 110 includes an imaging module and one or more LED light sources for viewing the organ or cavity into which it is inserted. The tip assembly 110 also includes one or more fluid ports. The distal end of the cannula 120 can also be slightly bent as shown in bent region 122.

According to some embodiments, the cannula 120 includes a fluid channel which is fluidly connected to distal fluid port 132 at fluid hub and connection assembly 130. Port 132 includes a Luer fitting to facilitate leak-free connection of port 132 with various medical fluid components. The fluid channel or lumen in cannula 120 is also connected to a distal facing fluid port (orifice or port 1114 shown in FIGS. 11, 12A, and 12D-E) of tip assembly 110. According to some embodiments, wires running from the LED light sources and camera module in tip assembly 110 pass through a separate channel in cannula 120. Although no dedicated working channel is provided in this example, an endoscopic guide wire can be passed through the fluid channel in some applications.

The endoscope 100 includes a handle portion 140 that is sized and shaped in a pistol-like fashion for easy grasping by the endoscope operator (e.g. doctor or other medical professional). A display module 150 is rotatably mounted on handle 140 via bearing 154 which can be a plain bearing made of plastic, and a rubber coated hinge 152. As can be see in the dotted outlines in FIGS. 1 and 2, the display module 150 can tilt relative to the handle 140 and can rotate about axis 156 relative to handle. 140. Also visible on handle 140 are image capture button 160 and power button 162. According to some embodiments handle 140 and display module 150 are configured to be re-usable and make up reusable portion 102. The fluid hub and connection assembly 130, cannula 120 and tip assembly 110 make up single-use portion 104 and are made at a relatively low-cost and are intended to be disposed of after a single-use. By making the tip, cannula, fluid hub all single-use, stringent decontamination and disinfection procedures as well as the risk of cross-contamination and hospital acquired diseases can be significantly lessened or avoided. According to some embodiments the disposable, single-use portion (portion 104 shown in FIGS. 3A and 3B) is sterilized, for example, during production and is provided to the user in a sealed sterilized pouch, for ease of storage and handling. Shown in FIGS. 1 and 2 are various dimensions that have been found to be practical for use in some applications, although other dimensions may be used for various applications. The camera module in the tip assembly can have a wide angle of view, such as 140 degrees in this example.

FIGS. 3A and 3B are perspective and side views showing aspects of attachment and detachment of single-use and reusable portions of a handheld endoscope, according to some embodiments. The single-use portion 104 and reusable portion 102 attach mechanically primarily via mating mechanical connectors 320 and 322. Electrical connection is made via separate mating electrical connectors 310 and 312. As can be seen in FIG. 3B, in this example the two portions 102 and 104 are attached via translation vertically towards each other. Note that in this example, on assembly 130 the electrical connector 310 and mechanical connector 320 are both separated from the fluid hub 300 that provides fluid communication between fluid port 132 and the fluid channel/lumen of cannula 120. This separation allow for easy and adequate fluid sealing to prevent fluid from fluid hub 300 from penetrating internally towards connectors 310 and 320 and also allows some protection against any exterior fluid, for example from fluid port 132 from reaching and possibly compromising electrical connectors 310 and 312. Also, the separation between mechanical connector 320 and fluid hub 300 allows for a sleeve bearing 330 to allow for rotating of cannula 120 relative to the proximal portion of assembly 130. The physical separation of the fluid hub 300 and the mechanical and electrical connectors 320 and 310 also provide additional assurance against accidental contamination from fluid hub 300 to the re-usable portion 102. As will be described in further detail infra, the difference between d1 and d2, or the separation between the electrical and mechanical connectors 310 and 320 allows for the insulated electrical cable to pass intact though the "housing" formed by fluid hub 300, the sleeve bearing 330 and the mechanical connector 320. Since the electrical connector 310 is positioned outside the fluid-containing "housing," the electrical connections between the cable and the connector can be made outside the housing as well. According to some embodiments, the distances d1 and d2 are about 70 mm and 35 mm respectively. According to some embodiments, both distances d1 and d2 are at least 20 mm and according to some other embodiments both distances d1 and d2 are at least 15 mm.

Figure 4:
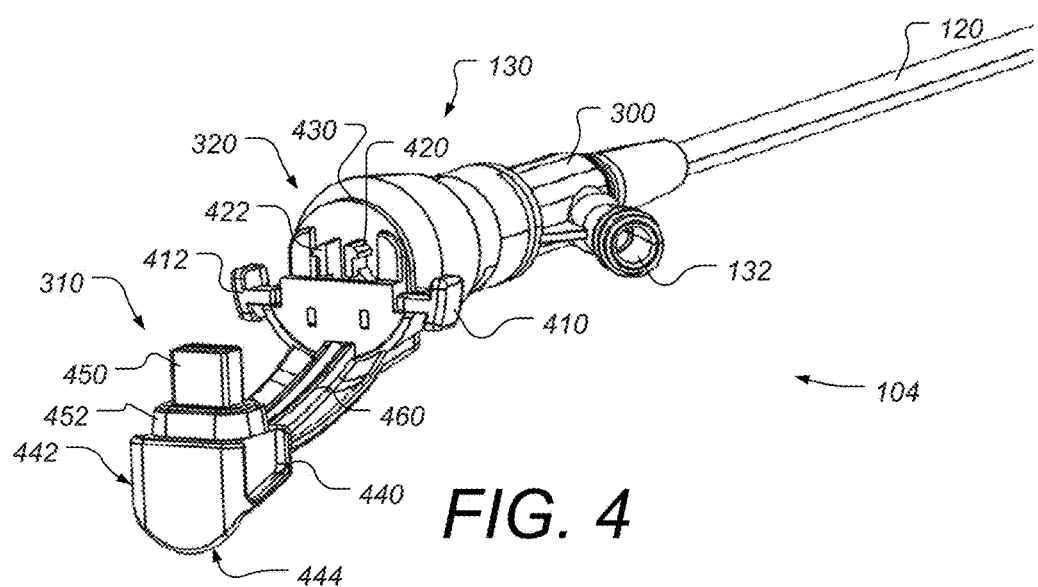
FIGS. 4 and 5 are perspective views showing further detail of mechanical and electrical connectors between single-use and reusable portions of a handheld endoscope, according to some embodiments.
Figure 5:
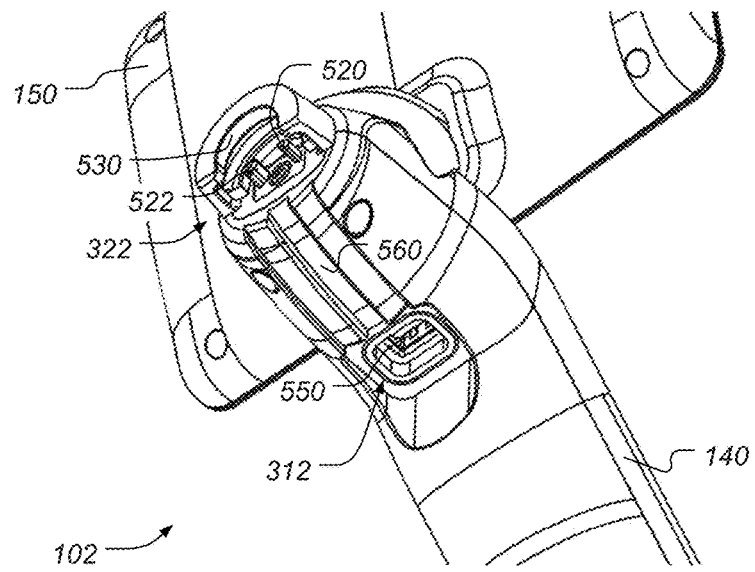

FIGS. 4 and 5 are perspective views showing further detail of mechanical and electrical connectors between single-use and reusable portions of a handheld endoscope, according to some embodiments. It can be seen that mechanical connector 320 includes a flat disk protrusion 430 that mates into a semi-circular slot 530. In order to further orient and lock the mechanic connectors 320 and 322 in a mating position, spring-loaded tabs 420 and 422 are configured to be pushed past protrusions 520 and 522 and then lock above them. In order to detach or un-mate single-use portion 104 from reusable portion 102, buttons 410 and 412 are simultaneously pushed inwards (towards each other) which pushes tabs 420 and 422 towards each other such that they can slip past protrusions 520 and 522. Electrical connector 310 on single-use portion 104 includes a male electrical connector 450 that electrically mates with female socket 550 on connector 312. According to some embodiments 20-pin mini-display port type connectors are used, although many other types of electrical connectors can be used. The electrical connector 310 is configured to be pushed into a mating recess on handle 140 by pushing upwards on pad 444. While mated, a ridge 460 that includes a slot for the insulated electrical cable fits into a slot 560 on the bottom of handle 140. To detach or un-mate single-use portion 104 from reusable portion 102, two shelves 440 and 442 can be gripped to pull connector 310 away from connector 312 in a downwards direction. Also visible in FIG. 4 is an elastomer o-ring 452 that aids in forming a seal with connector 312.

FIGS. 6A and 6B are top views illustrating further aspects of the rotatable display module on a handheld endoscope, according to some embodiments. A feature that is facilitated by positioning the display module off-axis (i.e. away from the central longitudinal axis of the cannula) is the ability to provide relatively wide angles of rotation for the display module. Such wide rotating angles increase ergonomics and usability for a wide range of users, procedures, and patient anatomies. FIG. 6A depicts the display module being rotated in a dock-wise direction such that it faces to the operator's left side, while FIG. 6B depicts the display module being rotated in a counter clock-wise direction such that it faces to the operator's right side. Such side to side rotation can be useful, for example to allow the display to be viewable by someone located to the operator's left or right sides. According to some embodiments, the display module can be rotated such that it faces away from the operator, such as shown in FIG. 6A. This may be useful, for example, to provide a view to the patient, or someone else located opposite to the operator. According to some embodiments, endoscope is configured to allow the display module 150 to be rotated 180 degrees or more in at least one direction (for example to allow for patient viewing) and to be rotated in 90 degrees or more in the other direction (for example to allow for side viewing). In the example shown in FIGS. 6A and 6B, the display module can be rotated past 180 degrees in the clockwise direction (as shown in FIG. 6A) and past 90 degrees in the counterclockwise direction (as shown in FIG. 6B). Other angles of rotation can be selected as desired or needed.

FIGS. 7A and 7B are a side view and perspective views of a cannula used on a handheld endoscope, according to some embodiments. The cannula 120 can be extruded and made of a nylon material such as nylon 12 (e.g. Grilamid® L25). The distal end of cannula 120 can include a bent region 122 which is beneficial for certain applications and can effectively increase the field of view of the camera fixed to the distal tip when the endoscope is rotated about its central longitudinal axis. FIG. 7B shows a further detail of the proximal region where cut out 710 is made to make a fluid connection between lower, fluid lumen 720 and the distal fluid port 132 of fluid hub 300 (shown in FIGS. 1-4, etc.). Also visible in FIG. 7B is the upper lumen 730 through which an insulated electrical cable (not shown) is run. According to some embodiments, the cannula 120 can be made such that its stiffness is not constant along its length. For example, it may be useful in some clinical applications to provide a cannula that is more flexible towards the distal tip and stiffer towards the handle. In such cases the cannula 120 can be made from a multi-durometer tubing such as a multi-duro Pebax® or Grilamid®.

Figure 8C:
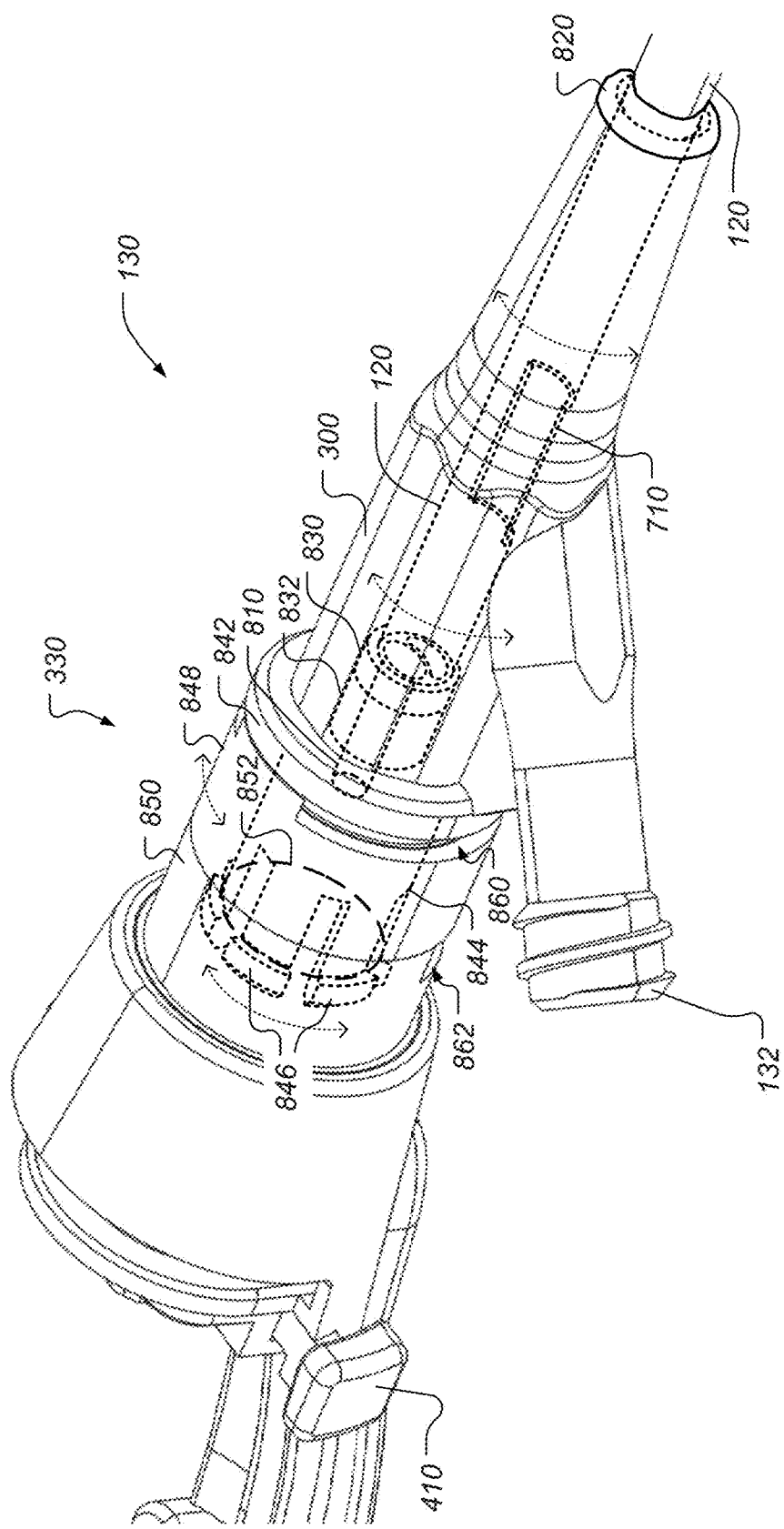

FIGS. 8A, 8B and 8C are top, side and perspective views illustrating further aspects of the fluid hub and connector assembly used on a handheld endoscope, according to some embodiments. Visible in FIGS. 8A and 8B is the proximal portion of cannula 120 inserted into fluid hub 300 of assembly 130. Close to where the fluid tube from port 132 meets the body of fluid hub 300, the cannula 120 includes cut-out portion 710 that forms an opening from the fluid channel/lumen within cannula 120 to the interior portion of fluid hub 300. The fluid hub 300 is sealed at its distal end to the outside of cannula 120 using techniques such as UV cured glue 820 that prevents any fluid in fluid hub 300 escaping around the seam between the outer surface of cannula 120 and the inner surface of the distal end of the housing of fluid hub 300. On the proximal end a fluid tight seal is also formed to prevent fluid passing proximally from fluid hub 300. According to some embodiments, an o-ring 830 and a fluid limiter 832 are positioned around the insulated electrical cable 810 at is passes out of the proximal end of cannula 120. A UV cured glue 822 can also be used to further provide a fluid-tight seal preventing any fluid leakage in the proximal direction on the inside of assembly 130.

Insulated cable 810 includes a plurality of further insulated electrical conductors for sending power to the camera and LEDs in the distal tip and signals back to electronics in the handle. Cable 810 emerges from the upper lumen (lumen 730 shown in FIG. 7B) of cannula 120. Cable 810 passes through sleeve bearing 330 and past the lower portion of mechanical connector 320. The fluid hub 300, sleeve bearing 330 and the mechanical connector 320 can be thought of as a "housing" which contains fluid within the fluid hub 300. Insulated cable exits this "housing" proximally through the lower portion of the mechanical connector 320 while its insulation is intact. The insulated electrical cable rests in a groove within ridge 460 (visible in FIG. 4). The insulated cable is terminated within electrical connector 310, where a plurality of the inner conductors 812 of cable 810 are bonded to male connector 450 as shown. The bonding can use solder or alternatively other techniques can be used to electrically connect inner conductors 812 to the appropriate portions of connector 450 as is well known. According to some embodiments, the outer insulation of cable 810 remains continuous and intact through the entirety of lumen 730 of cannula 120, through the fluid hub 300, sleeve bearing 330 and out of the "housing" through the lower portion of mechanical connector 320. Providing a continuously insulated, splice-free electrical cable facilitates prevention of shorts and other potential electrical faults due to fluid coming into contact with the inner conductors of the cable. Note that nowhere within the "housing" formed by the fluid hub 300, bearing sleeve 330 and mechanical connector 320 are any un-insulated electrical conductors exposed. Therefore, even if the fluid hub sealing means (e.g. o-ring 830, fluid limiter 832 and glue 822) were to fail there are no exposed conductors for the leaked fluid to come into contact with within the "housing." This is in contrast to designs where the mechanical and electrical conductors are in the same location, where it may be impractical to provide continuous, splice-free housing since electrical connections between the cable since at least a portion of the electrical connector may be positioned inside the same "housing" as the fluid hub.

FIG. 8C is a perspective view showing further detail of a fluid hub and connector assembly 130 on a handheld endoscope, according to some embodiments. The housing of fluid hub 300 rotates along with cannula 120. A portion of the housing of hub 300 includes ridge 842 and tube 844 that also rotate with cannula 120. The most proximal end of tube 844 includes a plurality of bendable latches 846. The stationary portion (i.e. not rotating along with cannula 120) of assembly 130 includes outer sleeve 850 that has an inner ridge 852 shown in dashed line. According to some embodiments, a partially rotating ring 848 is provided to facilitate an increased range of rotation for cannula 120. In such cases, the partially rotating ring 848 has distal slot 860 into which a proximally extending tab off of ridge 842 is disposed. During rotation of cannula 120, the tab of ridge 842 moves freely within slot 860 while ring 848 remains stationary until the tab of ridge 842 contacts one of the slot ends. After the tab of ridge 842 contacts an end of slot 860, and fluid hub 300 is rotated further, the ring 848 begins to rotate along with the fluid hub 300 and cannula 120 while a proximally extending tab on ring 848 slides along slot 862 formed in sleeve 850. When the tab of ring 848 contacts an end of slot 862 then no further rotation of cannula 120 is allowed. The tab and slots arrangement prevent rotation beyond a predetermined amount. In cases where a partially rotating ring 848 is not employed, a slot and tab arrangement can provide slightly less than 360 degrees of rotation (e.g. slightly less than 180 degrees in either direction). In cases where a partially rotating ring 848 is employed rotation can be limited to a full 180 degrees or more in either direction. Note that when setting the predetermined amount of rotation, care should be taken so that cable 810 does not undergo undue stress from twisting.

During assembly, the inner tube 844 and bendable latches 846 of fluid hub 300 are pushed into ring 848 and outer sleeve 850 which bend the latches 846 radially inwards. When the latches 846 pass the inner ridge 852 they spring back to their radially outward position as shown in FIG. 8C. The inner tube 844 and cannula 120 are then able to rotate as shown by the dotted arrows. Motion parallel to the main longitudinal axis of the cannula is prevented by the latches 846 against inner ridge 852 as well as by ridge 842 against the distal end of ring 848 which abuts the distal end of outer sleeve 850. Also visible in FIG. 8C in dotted outline is the portion of cannula 120 and cut out 710 that reside within fluid hub 300. A portion of cable 810 is also shown emerging from the proximal end of cannula 120.

It has been found that such configurations combined with the separation between the fluid hub, mechanical and electrical connectors allows for a relatively straightforward and inexpensive assembly process. For example, in some cases more complex can costly assembly techniques such as bonding together two halves of the fluid hub shell can be avoided.

Figure 9A:
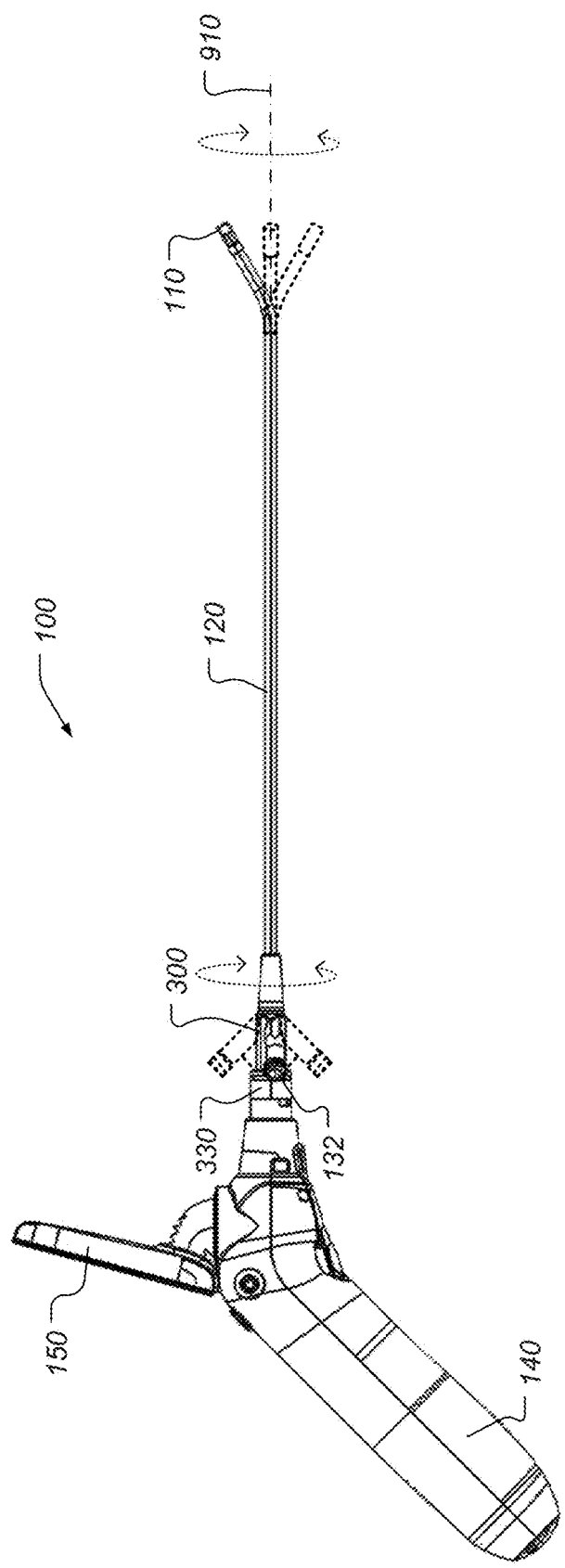
FIGS. 9A and 9B are side and front views illustrating further aspects of a rotatable cannula used on a handheld endoscope, according to some embodiments.
Figure 9B:
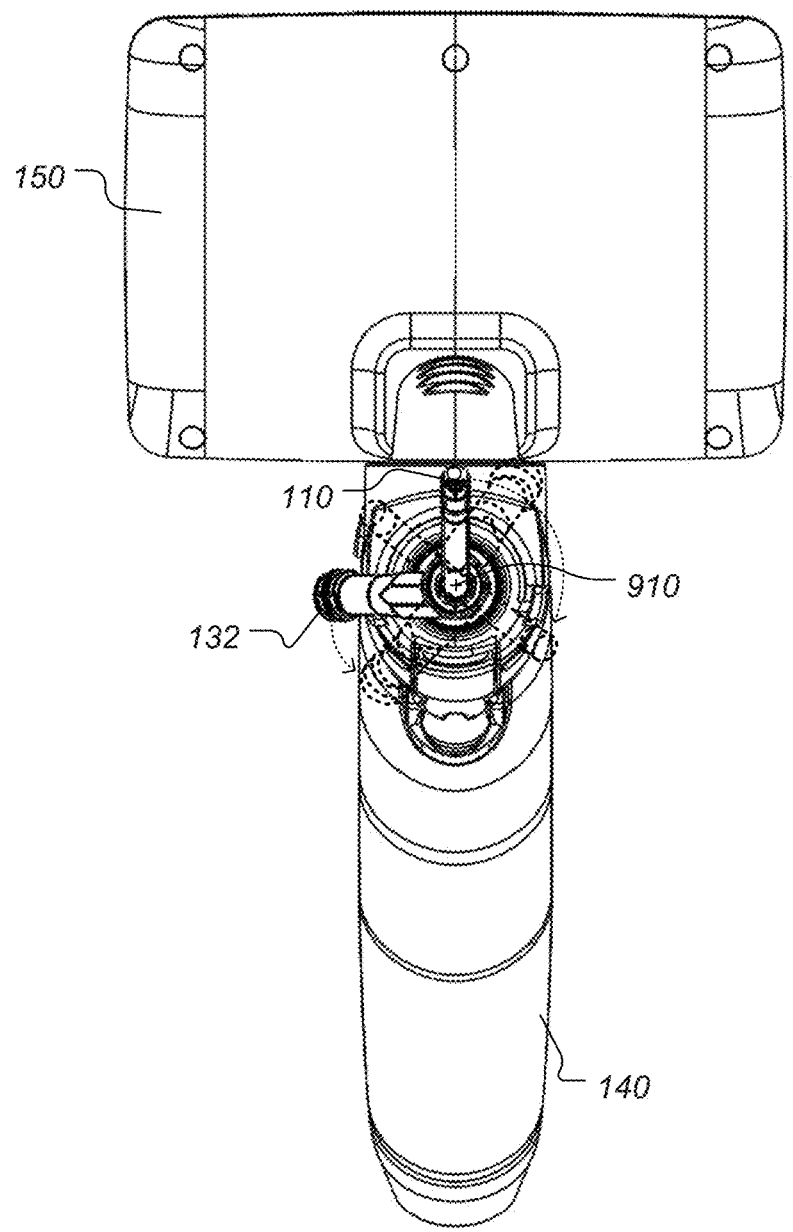

FIGS. 9A and 9B are side and front views illustrating further aspects of a rotatable cannula used on a handheld endoscope, according to some embodiments. Cannula 120 along with the distal tip 110 and fluid hub 300 are rotatable about the main axis 910. The portion of assembly 130 that rotates with cannula 120 includes the fluid port 132, fluid hub 300 and inner tube 844 (shown in FIG. 8C) that forms the inner portion of sleeve bearing 330. As described supra with respect to FIG. 8C, rotation of cannula 120 can be limited so that the internal electrical cable does not undergo undue stress from twisting. In one example starting from a "neutral" position shown in FIGS. 1 and 2, and in solid lines in FIGS. 9A and 9B, the cannula 120 can be rotated about 180 degrees in either direction (i.e. clockwise and counter clockwise as viewed in FIG. 9B). According to some other embodiments, an asymmetrical rotation pattern can be implemented in sleeve bearing 330 such as 270 degrees in one direction and 90 degrees in another direction. Many other combination can be implemented, to improve ergonomics for various situations (i.e. various users, types of procedures, and patient anatomy variations). According to some embodiments, the rotation is limited so as not to put undue stress on the internal electrical cable.

Figure 10A:
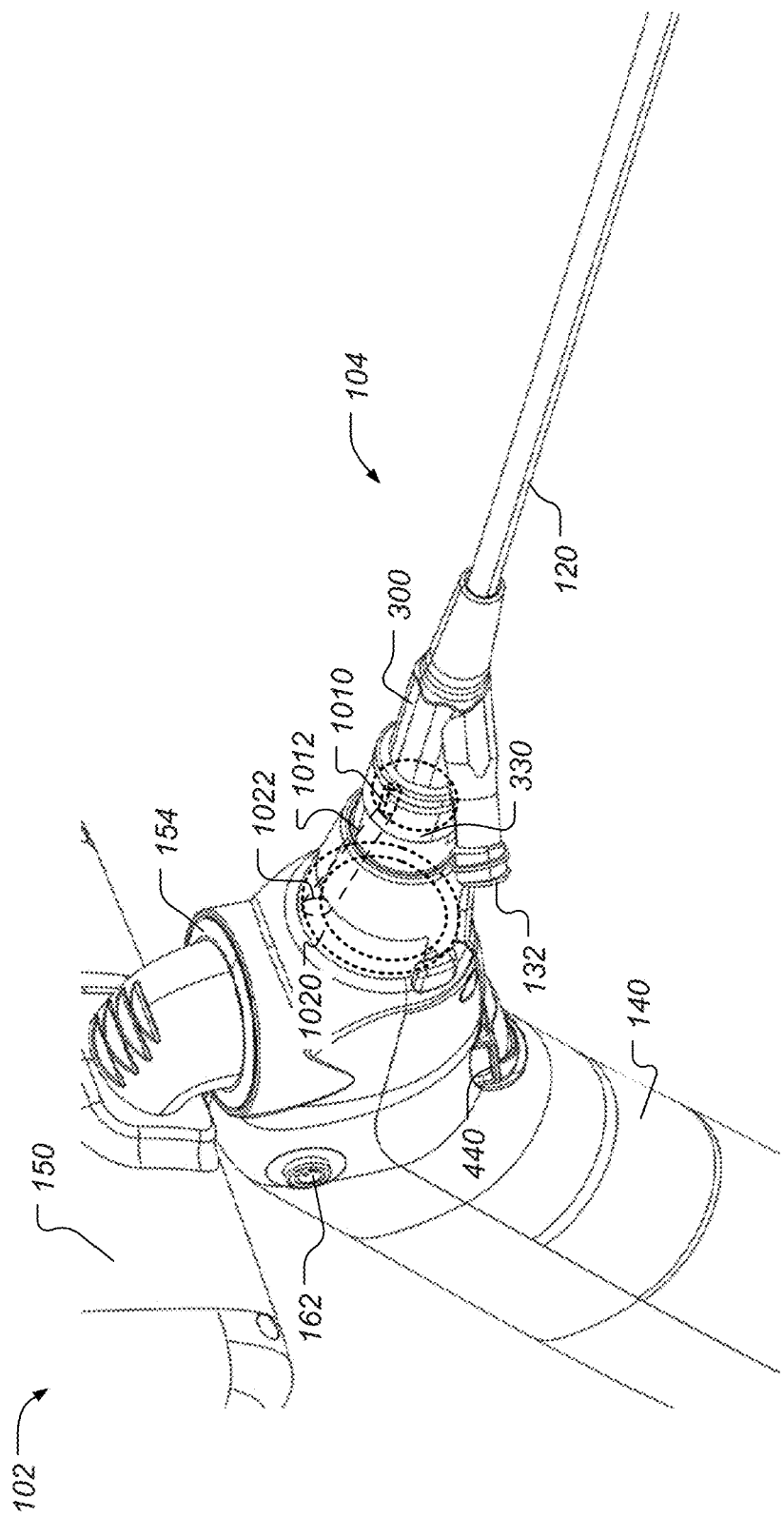
FIGS. 10A and 10B are perspective views showing aspects of light sources and sensors used to detect cannula rotational position on a handheld endoscope, according to some embodiments.
Figure 10B:
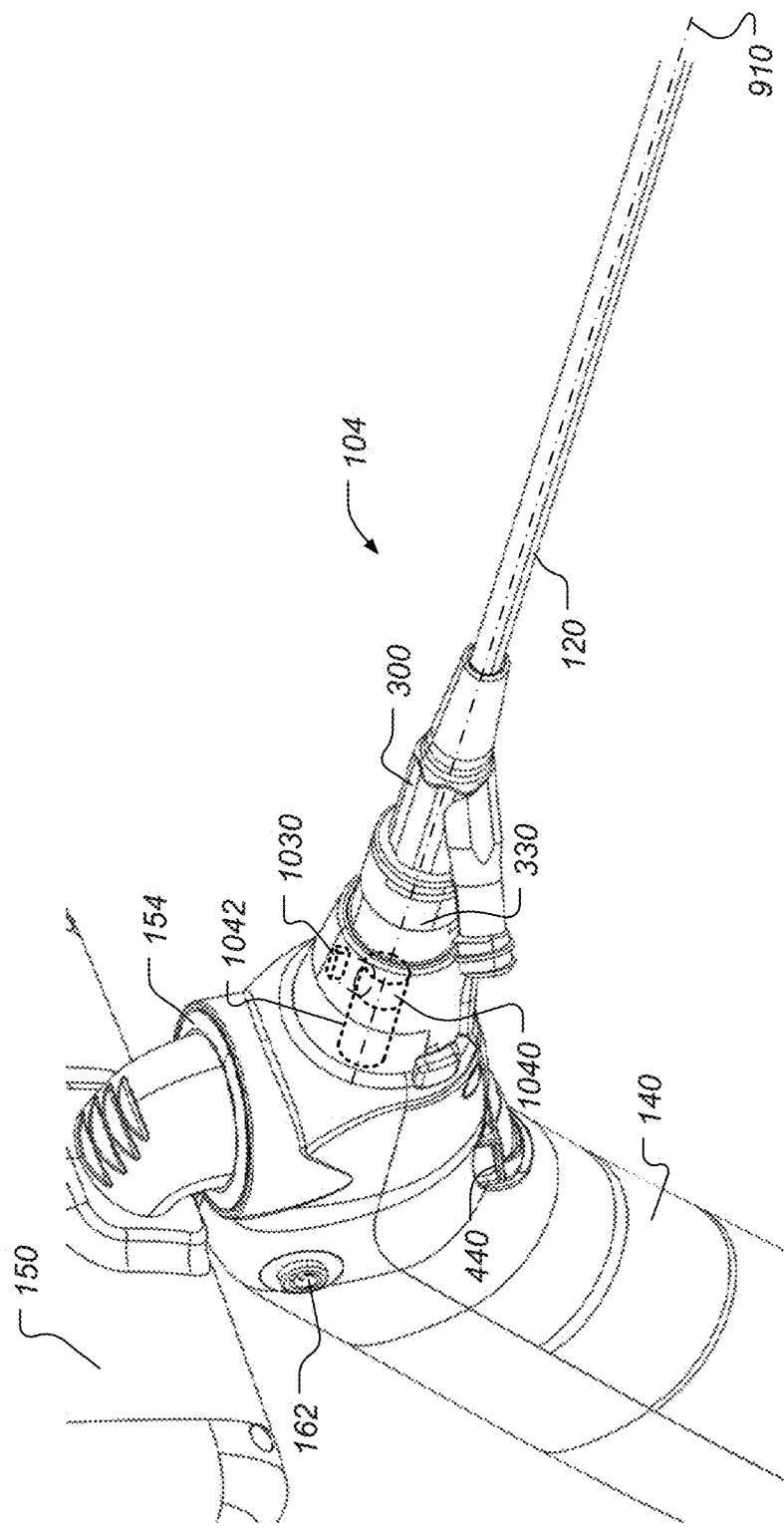

FIGS. 10A and 10B are perspective views showing aspects of light sources and sensors used to detect cannula rotational position on a handheld endoscope, according to some embodiments. As discussed supra, the cannula 120 and distal tip 110 can be rotated to visualize the target objects. However, because the display 150 is on the handle 140 that does not rotate, images or video displayed on display 150 from the camera module in the rotated distal tip 110 may not be correctly orientated with respect to target object of the object. According to some embodiments, simple low-cost fixtures that use an LED and light sensor can be used to detect the rotational position of the cannula 120 relative to the handle 140. The detected rotational position is then input to a software algorithm configured to reorient the image displayed on display module 150 such that a correctly oriented image is displayed to the operator. In FIG. 10A, a positional LED (P-LED) 1010 is placed on the proximal end the single-use portion 104 of the endoscope. In particular the P-LED 1010 can be incorporated into the inner tube 844 portion (shown in FIG. 8C) such as near or on one of the latches 846 (also shown in FIG. 8C). The P-LED 1010 is configured to be somewhat focused and collimated to form a light beam 1012. According to some embodiments, some or all of assembly 130 can be made of a transparent or translucent material. A light sensor ring 1020 is mounted on the reusable handle 140, such as within or just behind mechanical connector 322 (shown in FIG. 5). The light sensor ring 1020 provides a signal to a video processing DSP in handle 140 to indicate the angle of the light beam (which indicates the relative rotational position of the cannula 120). A video processing algorithm is configured to correct for the cannula rotational position when displaying video or images on display module 150. According to some embodiment the video processing algorithm is configured to rotate the image in a video buffer prior to display on the display module 150. According to some embodiments, the collimated beam 1012 is generated by P-LED 1010 using a slit formed in its proximal end. FIG. 10B is another example arrangement that can be used to detect the rotational position of the cannula. In this example, the P-LED 1030 is mounted such that it rotates with cannula 120 and is configured to direct a focused light beam radially inwards towards axis 910 such that its relative rotational position can be detected by light sensor ring 1040. In this case, light sensor ring 1040 is mounted on a post 1042 that protrudes from the handle 140 and therefore does not rotate with cannula 120.

Figure 11:
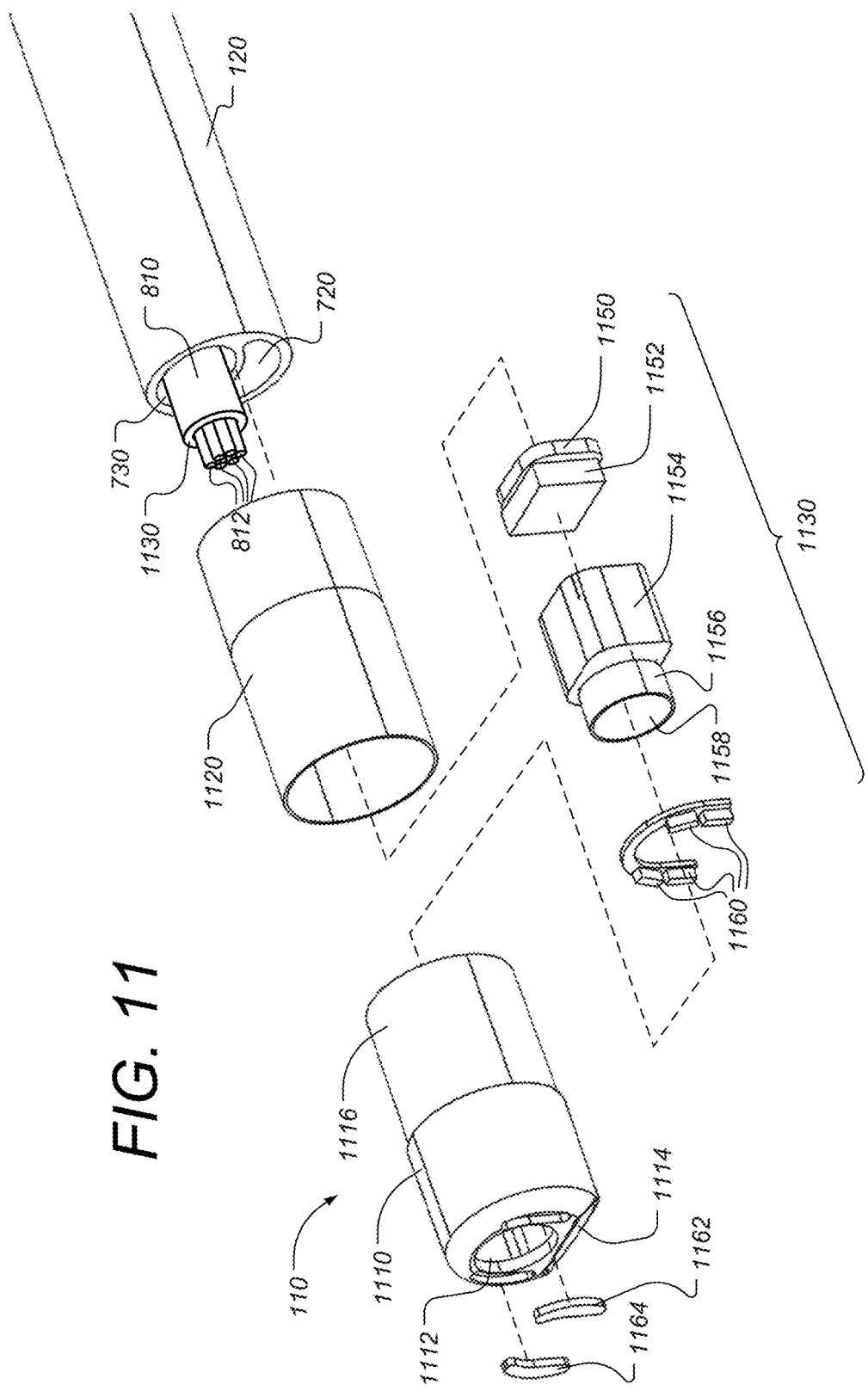
FIG. 11 is an exploded diagram showing various components of a distal tip used on a handheld endoscope, according to some embodiments.

FIG. 11 is an exploded diagram showing various components of a distal tip used on a handheld endoscope, according to some embodiments. Cannula 120 is shown with its upper lumen 730 used to carry cable 810 and lower lumen 720 used to convey fluid. The cable 810 emerges from upper lumen 730. Cable 810 has outer insulation layer 1130 surrounding a plurality of inner conductors 812. Each of the inner conductors 812 have their own insulation. Although 6 conductors 812 are depicted in this example, other numbers of conductors can be used depending on the needs to of cameral module and LEDs. The cannula 120 and tip housing 1110 are held together using a sleeve 1120 that is dimensioned to fit around both the outer surface of the distal end of cannula 120 and the proximal end 1116 of tip housing 1110. According to some embodiments, sleeve 1120 is made of stainless steel, although other material can be used. The three pieces, cannula 120, sleeve 1120 and tip housing 1110 can be glued together using, for example, a U-V cured bonding glue. Some or all of the conductors 812 are bonded to the printed circuit board (PCB) 1150. According to some embodiments, a relatively strong bonding technique, such as solder, is used to attach the conductors 812 to PCB 1150. Such strong bonding has a benefit of further reducing risk that the portions of the tip assembly 110 become separated from the cannula during a procedure. Sensor 1152 is mounted on PCB 1150. A holder 1154 sits around sensor 1152 and a light shield 1156 further surrounds the lens system and dust cover 1158.

According to some embodiments, a plurality of LEDs 1160 are mounted to a horseshoe-shaped LED board that surrounds the distal end of the lens system 1158. According to some embodiments, two light-guide lenses 1162 and 1164 are inserted and bonded to recesses in the distal end of tip housing 1110. The lenses 1162 and 1164 are configured to provide an even more uniform beam pattern to facilitate higher quality images and video of the patient's tissues. Although 4 LEDs 1160 are shown in FIG. 11, other numbers of LEDs can be used around the periphery of lens system 1158 such as 1, 2, 3, 4, 5, 6 or more LEDs. By using 4 LEDs, its has been found that a relatively uniform beam pattern can be produced. By positioning the LEDs inside the housing 1110 instead of flush with the distal surface, the LEDs are in a sense "encapsulated" in that they do not contact the patient tissue an are well sealed from fluid such as saline. It has also been found that the translucent shell provides some useful light dispersion for a more wide spread illumination either with our without the use of lenses 1162 and 1164. Also, recessing the LEDs as shown frees up some space on the distal surface. Finally, the assembly process is simplified when locating the LEDs inside the housing 1110.

The components 1130 are positioned within an upper cavity (cavity 1216 shown in FIG. 12B) of tip housing 1110. The tip housing 1110 can be molded from a transparent material such as polycarbonate but other easy to mold materials could be used instead. When assembled, the front of lens system 1158 sits flush with the distal end of tip housing 1110 through lens orifice 1112. A lower orifice 1114 is provided to allow for fluid communication with lower lumen 720 of cannula 120. Note that port 132, lumen 720 and orifice 1114 can be provide fluid in-flow (i.e. flowing fluid out of the endoscope and into the patients organ or cavity and/or fluid out-flow (i.e. flowing fluid out of the patients organ or cavity and into the endoscope).

It has been found that forming the cannula and distal tip parts separately has significant manufacturing advantages. The cannula can be extruded while the distal tip can be molded. Furthermore post-extrusion preparation of the extruded cannula is very straightforward, using only a bending and a simple cut made on its proximal end (e.g. as shown in FIG. 7B).

Figure 12A:
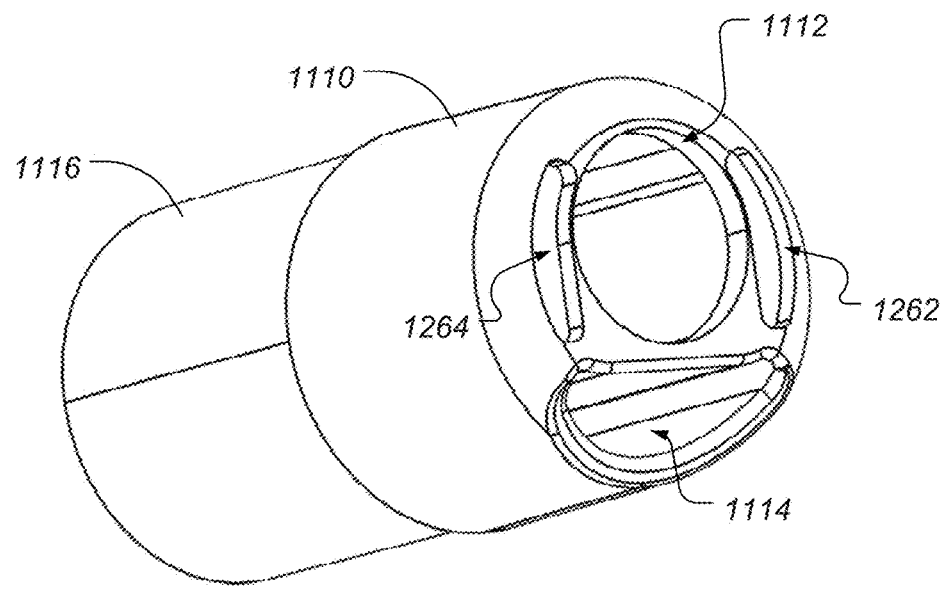
FIGS. 12A-12I are diagrams illustrating further details of a molded distal tip housing for use on a handheld endoscope, according to some embodiments.
Figure 12B:
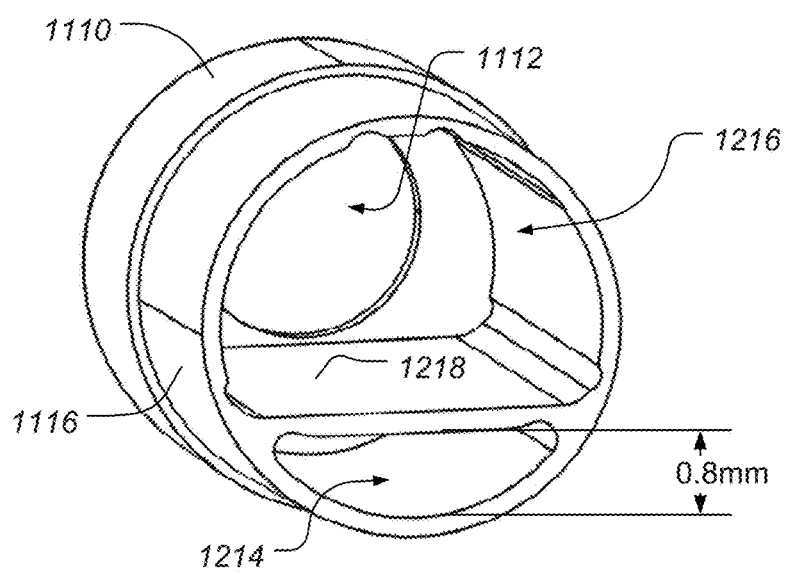
Figure 12C:
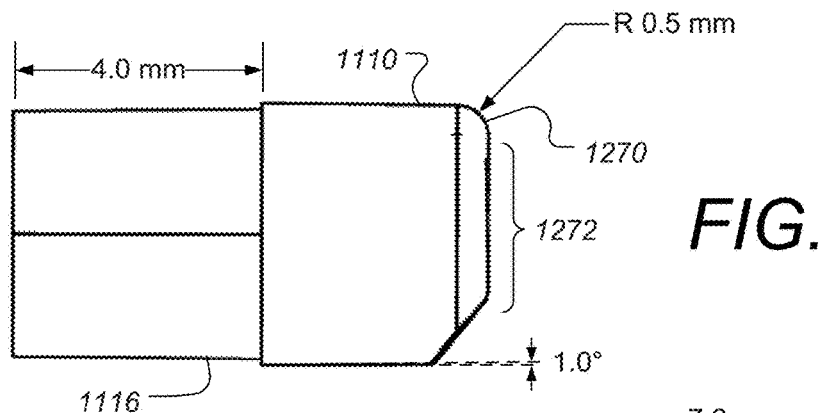
Figure 12D:
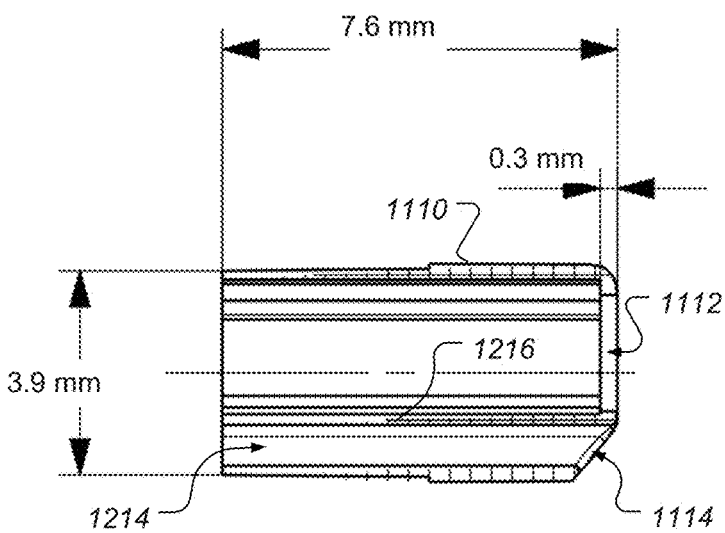
Figure 12E:
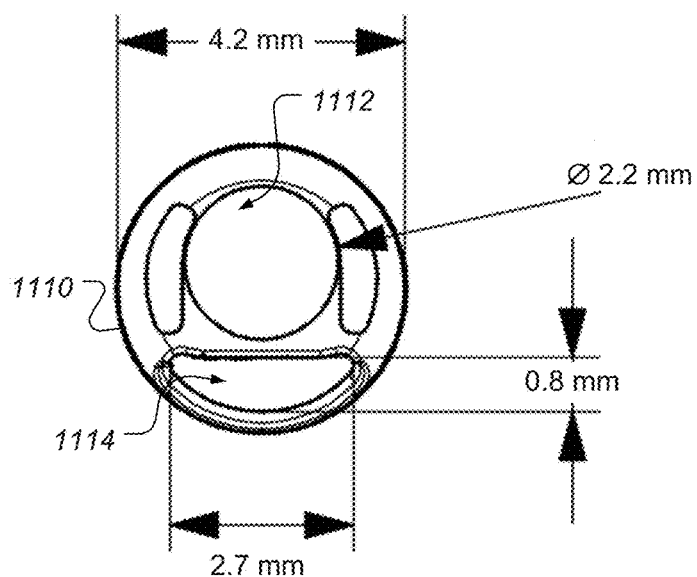

FIGS. 12A-12I are diagrams illustrating further details of a molded distal tip housing for use on a handheld endoscope, according to some embodiments. In FIG. 12A, the recesses 1262 and 1264 are visible into which the lenses 1162 and 1164 are inserted. Also more clearly visible is the lower orifice 1114 through which fluid can pass into or out of the patient. As can be seen from FIG. 12B, the inner part of housing 1110 is separated into two cavities 1214 and 1216 that are separated by wall 1218. FIGS. 12C-12E show further dimensions according to an example embodiment. According to some embodiments, the distal outer edge 1270 rounded to facilitate insertion in/though tissue passages and alleviate tissue contact issues. When inserting the endoscope into and through passages such as the urethra, trachea or blood vessels, it is desirable that the outer distal edge 1270 of the distal tip should be rounded since that region of the distal tip both contacts and dilates the tissue passage. In such cases, the central portion 1272 of the distal tip can be made less rounded or flat. Making the central portion 1272 less rounded or flat has been found to enhance imaging characteristics over a more spherical overall tip since the camera and illumination is not or significantly less impaired. In the case shown, the distal end of lens system 1158 (shown in FIG. 11) is a flat glass dust cover and sits flush with the remainder of central portion 1272 of housing 1110. FIG. 12C also shows that outer surface of housing 1110 can be made slightly tapered such that the outer dimension decreases slightly towards the distal tip. In the example shown an approximately 1 degree taper has been found to be useful for insertion in urological applications.

Figure 12F:
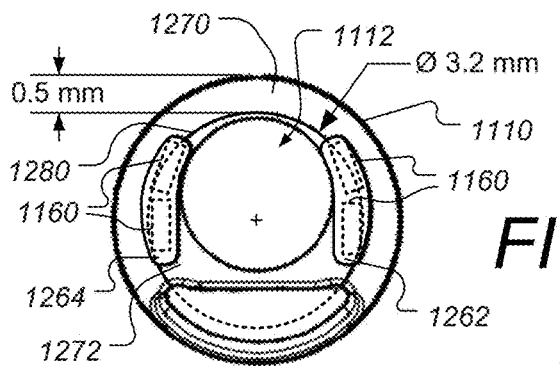

FIG. 12F shows further detail of the rounding at the distal outer edge 1270, according to some embodiments. The rounded portion 1270 of the distal edge can be seen in this example to extend smoothly and continuously from the outer peripheral edge (i.e. sidewall) of housing 1110 to an inner circle 1280. Within circle 1280 the distal tip is less rounded or flat in central portion 1272 (also visible in FIG. 12C). As mentioned a flat central portion 1272 may be advantageous for imaging quality by the lens and camera module. Note the rounded portion 1270 can extend over a portion of (i.e. partially overlap) the LEDs 1160. Mounting the LEDs in a recessed location within a separate translucent molded tip piece allows for greater freedom and generally larger area for a continuous smooth rounded portion 1270. In the example shown in FIG. 12C, the circle 1280 has a diameter of about 3.2 mm such that the rounded portion 1270 extends about 0.5 mm or about 25% of the overall radius of the distal tip. By making the distal tip from a separate molded housing piece 1110, as opposed to attempting to shape the extruded cannula material, a smooth continuous surface as shown can be achieved which facilitates insertion into tissues and tissue passageways. It has been found that providing a smooth continuous extended rounded portion 1270 such as shown and described is useful for insertion in urological applications to reduce or eliminate patient discomfort.

Figure 12G:
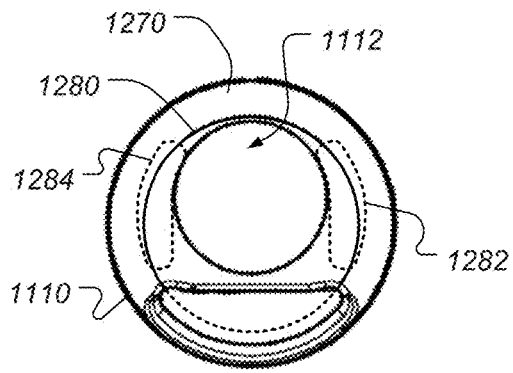
Figure 12H:
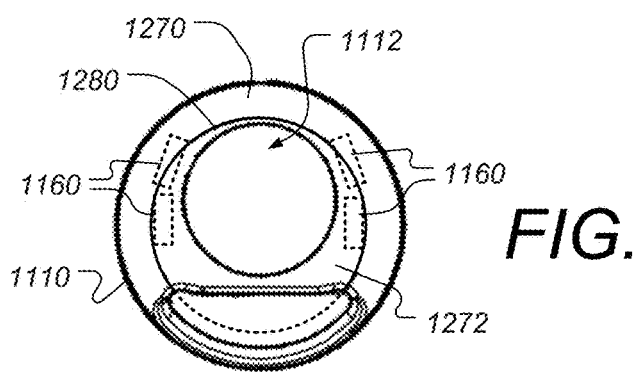
Figure 12I:
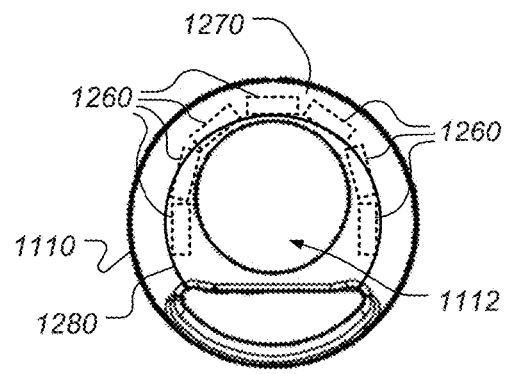

FIGS. 12G, 12H and 12I show distal tip configurations, according to some embodiments. In FIG. 12G, instead of separate light guide lenses 1162 and 1164 (shown in FIG. 11), textured regions 1282 and 1284 are provided which are configured to diffuse light from the recessed LEDs 1160 (shown in FIGS. 11, 12F and 12H). In some cases, no separate lenses and no textured regions are needed to provide adequately uniform illumination from the recessed LEDs. This case is shown in FIG. 12H, where light from LEDs 1160 emit through the smooth rounded surface of the regions 1270 and flat central portion 1272. FIG. 12I illustrates a case where other numbers of recessed LEDs are provided. Mounting the LEDs in a recessed location within the separate molded tip piece generally allows for greater flexibility in positioning locations and numbers of LED used. This in turn, allows for greater ability to provide suitable and uniform illumination for each intended application. In this example, seven LEDs 1260 are provided around the periphery of lens orifice 1112 (and lens system and dust cover 1158 shown in FIG. 11).

Figure 13:
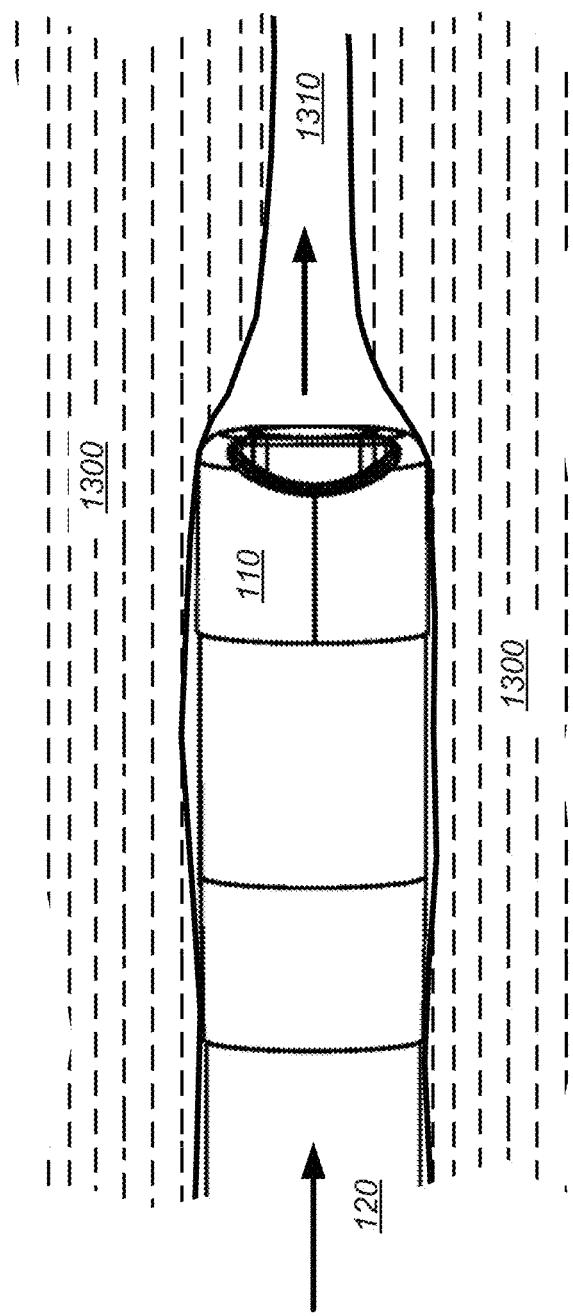
FIG. 13 is a diagram showing a handheld endoscope being inserted in a tissue passageway, according to some embodiments.

FIG. 13 is a diagram showing a handheld endoscope being inserted in a tissue passageway, according to some embodiments. The distal tip 110 and cannula 120 of the endoscope is being inserted in passageway 1310 (e.g. a urethra or blood vessel) within tissue 1300. As shown, the passageway 1310 is being dilated by the distal tip 110. The distal tip 110 has a rounded distal edge shape such as shown in FIGS. 12A-12E such that its outer distal edge 1270 is more rounded (i.e. smaller rounding radius) than the central portion 1272 of the distal tip, which is flat in some cases. It has been found that this rounding profile allows for both good tissue contact and dilation characteristics, and good viewing and illumination characteristics.

Figure 14:
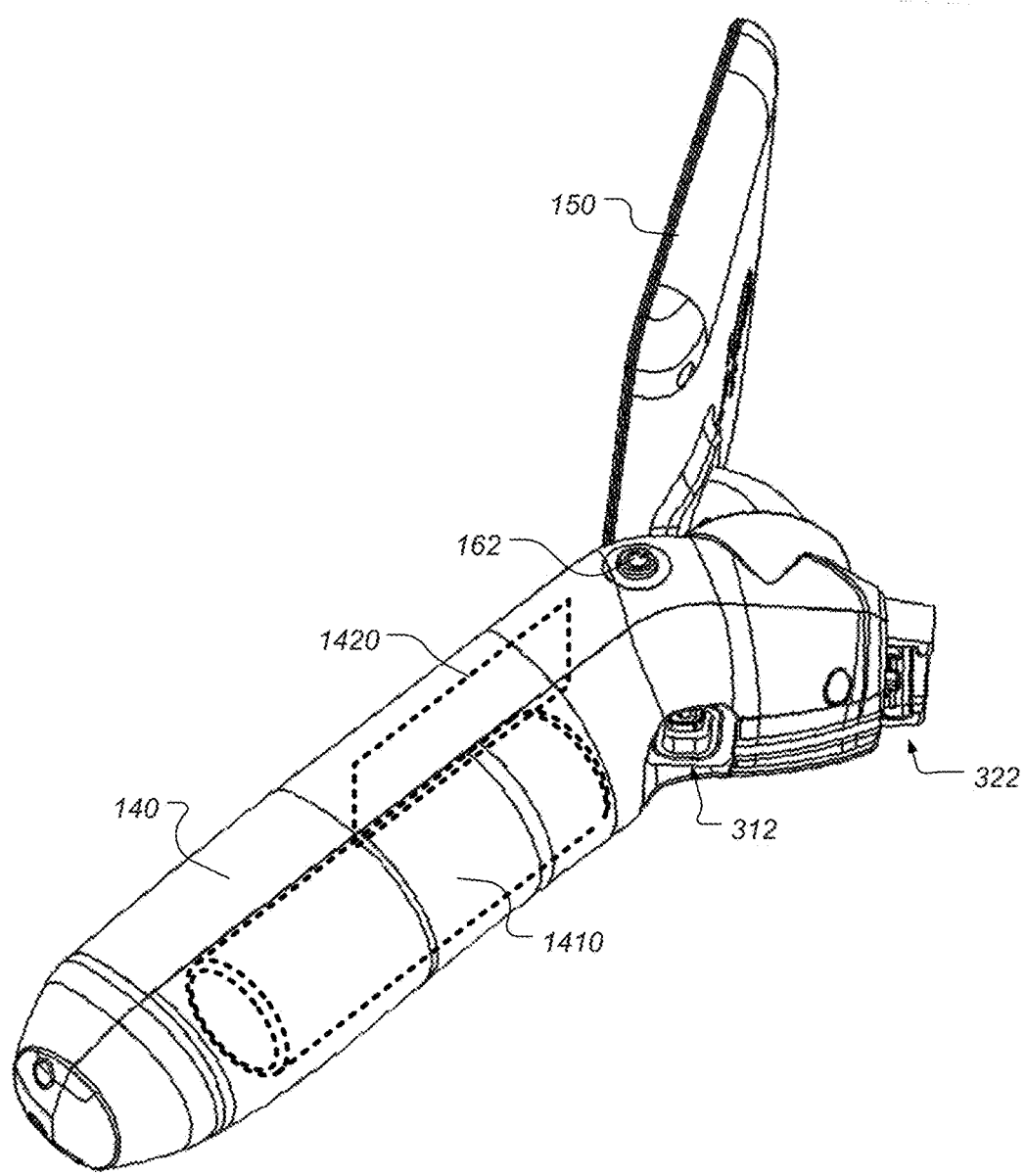
FIG. 14 is a perspective view of a reusable portion of a handheld endoscope, according to some embodiments.

FIG. 14 is a perspective view of a reusable portion of a handheld endoscope, according to some embodiments. Shown in dotted outline are the rechargeable battery 1410 and printed circuit board (PCB) 1420. The rechargeable battery is used to power the endoscope including the electronics on PCB 1420 and elsewhere, the display module 150 as well as the component in the distal tip assembly. The rechargeable battery 1410 can be recharged, for example using a charging cord or dedicated stand that make electrical contact to the handle via the electrical contact 312.

According to some embodiments, the portions of the endoscope that may be come in contact with a patient's tissue, such as the distal portion of cannula 120 and the tip assembly 110, are hydrophilic. This can be accomplished, for example, by treating those portions of the endoscope as is known in the art. According to some embodiments, after assembly and cleaning, the cannula 120 and tip assembly 110 are dipped into a hydrophilic solution and allowed to dry. Drying and solidification of the hydrophilic coating can be enhanced using an a humidity controlled oven at approx. 70 degrees C.

It has been found that when performing certain medical procedures with a endoscope having a rotatable cannula that the cannula is commonly rotated to a certain position followed by "holding" that rotational position for some time. In many cases this "rotate and hold" pattern is repeated several times during a given procedure. Is has been found useful to provide an amount of friction or drag in the rotating action such that the cannula remains in fixed orientation with the handle under friction until the user intends to cause relative rotation between the cannula and handle. At such time the friction is overcome to allow rotation between the handle and cannula to its new intended relative position. According to some embodiments, the "frictional fit" is such that rotation of the cannula relative to the handle starts only after the application of torque over a threshold that preferably is in the range of 0.04 N·m to 0.2 N·m and more preferably is at least 0.07 N·m. It has been found that a threshold torque value of about 0.1 N·m is practical for certain urological as well as other procedures. FIGS. 15A and 15B are perspective and cross-sectional views of a single-use portion of a handheld endoscope, according to some embodiments. An o-ring 1510 that is made of an elastomeric material such as silicon is positioned in a notch 1512 on the outer surface of tube 844 as is visible in FIG. 15A. The o-ring 1510 provides rotational friction between the cannula and the handle by introducing friction between the tube 844 (that is fixed to the fluid hub 300 and the cannula) and inner surface of outer sleeve 850. According to some embodiments the o-ring 1510 is 0.8 mm in thickness and has a diameter of about 8 mm. According to some embodiments other known techniques of introducing the desired amount of friction can be used instead of an o-ring. For example, the o-ring can be eliminated and friction between the outer surface of tube 844 and the inner surface of sleeve 850 can used to provide the desired amount of friction.

Thus, in some embodiments the endoscope comprises a single-use portion 104 that includes a cannula 120 that has a tip sub-assembly 110 at a distal region and an intermediate region that extends proximally from the distal region and ends at a proximal region. The cannula has proximal port in the form of a cutout 710, a distal port at lower orifice 1114, and a fluid lumen 720 connecting the two ports and a cable lumen 730 extending from the distal to the proximal regions. The single-use portion further includes a fluid hub and connection assembly 130 that comprises fluid hub 300 having a distal region to which the proximal region of cannula 120 is secured, an intermediate region with a fluid port 132 aligned with cutout 710, and a distal region rotatably secured to an outer sleeve 850 that has a mechanical connector 320 at an intermediate region and an electrical connector 310 on a cantilever support extending proximally from mechanical connection 320. The endoscope further comprises a reusable portion 102 comprising a pistol-grip handle 140, a video screen 150 mounted on the handle about two axes that are transverse to each other and to the long axis of cannula 120, a mechanical connector 322 at a distal region of handle 140 configured to lock and unlock by hand to mechanical connector 320, and an electrical connector 312 proximally spaced from the distal region of the handle and configured to connect and disconnect by hand with electrical connector 310. Fluid hub 130 together with cannula 120 rotates relative to outer sleeve 850 and thus relative to handle 140, over an angle defined by a rotation limiter that comprises one or more slot-and-tab mechanisms, for example a first slot 860 and a tab riding therein, and a second slot 862 and a tab riding therein. An angle encoder or position sensor, for example positional LEDs 1010 and light sensor ring 1020 provide an electrical signal to an electronic facility in handle 140 or video screen 150 operative to orient an image shown on screen 150 as a function of rotational positions of cannula 120 relative to handle 140

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

What it claimed is:

1. A hand-held endoscope comprising:
   a single-use portion having:
      a fluid hub and connector assembly comprising a mechanical connector, an electrical connector, and a fluid hub with a fluid port;
      wherein the mechanical connector is at an intermediate region of the fluid hub and connector assembly and is spaced a selected distance proximally from the fluid hub, and the electrical connector is at a proximal region of the assembly and is spaced proximally from the fluid hub by a distance greater than said selected distance; and
      a cannula secured to a distal region of the fluid hub and comprising (i) a video camera and a light source at a distal region thereof, (ii) a fluid port at a proximal region thereof in fluid flow communication with the fluid hub's fluid port, and a fluid port at the cannula's distal region, (iii) a fluid flow lumen between the cannula's fluid ports, (iv) an electrical cable lumen separated from the fluid flow lumen and extending between the cannula's distal and proximal regions, and (v) a splice-free cable extending from the video camera and light source to the electrical connector that is proximally spaced from the mechanical connector;
   a reusable portion comprising:
      a handle configured to be grasped by a user's hand;
      a video screen mounted on the handle and configured for rotational motion around two axes that are transverse to each other, to different orientations relative to the handle;
      a mechanical connector at a distal portion of the handle, configured to mate with the mechanical connector of the fluid hub and connector assembly to lock and unlock by hand the handle and the single-use portion to and from each other; and
      an electrical connector spaced proximally from the mechanical connector on the handle and configured to connect to and disconnect electrically the handle to and from the fluid hub and connector assembly by hand;
   said fluid hub and connector assembly further comprising:
      an outer sleeve integral with or affixed to the assembly's mechanical connector, wherein a proximal portion of the fluid hub is mounted to the outer sleeve for rotation together with the cannula relative to the assembly's mechanical connector; and
      a rotation limiter comprising a first slot at one of said outer sleeve and fluid hub and a first tab at the other, said first slot having stops to limit the angular extent of the first tab's travel in the first slot and thus to limit the angular extent of rotation between (i) the outer sleeve and the assembly's mechanical connector and (ii) the fluid hub and cannula;

said fluid hub being mounted to the outer sleeve in a fit configured to maintain the relative rotational positions of the handle and cannula until a torque threshold is met.

2. The endoscope of claim 1, in which the torque threshold is in the 0.04-0.2 newton meters (N·m) range.

3. The endoscope of claim 2, in which the torque threshold equals or exceeds 0.07 N·m.

4. The endoscope of claim 3 in which the torque threshold is 0.1 N·m.

5. The endoscope of claim 1 in which the fluid hub is mounted to the outer sleeve in a frictional fit.

6. The endoscope of claim 1, in which the fluid hub is sealed against proximal fluid flow at a location distal from the mechanical connector of the single-use portion, and said cable extends splice-free proximally from the location where the fluid hub is sealed to the location of the electrical connector of the single-use portion of the endoscope.

7. The endoscope of claim 1, in which said rotation limiter further comprises a ring mounted for limited angle of rotation relative to both of said outer sleeve and said fluid hub, wherein said first slot and first tab are at the ring and the fluid hub, and said ring and the outer sleeve comprise a second slot and a second tab that rides in the second slot and engages ends thereof to limit the relative rotation between the ring and outer sleeve, wherein the first and second slots and ends thereof are positioned to permit greater angle of rotation of the cannula relative to the outer sleeve and thus the handle than either of the slots alone.

8. The endoscope of claim 1, including an angle encoder configured to detect degree of rotation of the cannula relative to the handle, and an electronic facility operatively connected to the angle encoder and to the video screen and configured to rotate an image on the screen in relation to rotation of the cannula relative to the handle.

9. The endoscope of claim 1, in which the video screen is offset from a long axis of the cannula and rotates relative to the handle to positions including a position in which the screen faces the cannula's distal region to thereby facilitate visualization by a patient undergoing a procedure with the endoscope.

10. The endoscope of claim 1, in which the cannula's distal region is a molded housing for the video camera and light source while the cannula's more proximal regions are extruded.

11. The endoscope of claim 1, in which the cannula's distal region and at least an intermediate region of the cannula include a hydrophilic coating.

12. The endoscope of claim 1, in which the light source at the cannula's distal region comprises four or more LEDs recessed proximally from a front surface of the cannula's distal region, and a peripheral portion of a distal end of the cannula's distal region is rounded to facilitate insertion of the cannula in a patient's passage and movement of the cannula along the passage.

13. An endoscope comprising:
a reusable portion having a handle with a mechanical connector at a distal region, an electrical connector at an intermediate region, and a video screen mounted on the handle;
a single-use portion having:
a cannula with a video camera, a light source and a fluid port at a distal region, a fluid port at a proximal region, and a fluid lumen connecting the fluid ports and configured for fluid flow between the cannula's ports;
a fluid hub having a distal region secured to the proximal region of the cannula and a fluid port communicating with the fluid port at the cannula's proximal region for fluid flow;
an outer sleeve having a distal region to which a proximal portion of the fluid hub is rotatably mounted and further having a proximal region forming a mechanical connector releasably interlocking by hand with the reusable portion's mechanical connector to thereby interlock the single-use and reusable portions into said endoscope and an electrical connector proximally spaced from the mechanical connector;
a slot- and tab mechanism at said outer sleeve and fluid hub configured to limit the angle of rotation between the outer sleeve and the fluid hub;
a cable extending splice-free from the distal to the proximal regions of the cannula in a cable lumen separated from the fluid lumen, and thence through at least a part of the fluid hub and the outer sleeve and to the single-use portion's electrical connector; and
a seal at a proximal portion of the fluid hub configured to keep fluid from the fluid lumen and the fluid port of the fluid hub from moving in the proximal direction from the seal, thereby keeping the mechanical connectors of both the single-use and reusable portions and the electrical connectors of both the single-use and the reusable portions free of such fluid.

14. The endoscope of claim 13, in which the video screen is mounted for rotation between a proximally facing position and a distally facing position.

15. The endoscope of claim 13, further including a positional sensor configured to detect rotation between the handle and cannula, and a circuit coupled with the positional sensor and configured to rotate an image on the screen as a function of rotation detected by the position sensor.

16. The endoscope of claim 13, in which the cannula's distal region comprises a housing for said video camera and light source at a tip of the cannula and a metal sleeve affixing the housing to the remainder of the cannula.

17. The endoscope of claim 13, in which the handle comprises a pistol grip angled relative to a long axis of the cannula, and buttons controlling the video camera and light source at an upper region of the pistol grip.

18. The endoscope of claim 13 in which the mounting of the fluid hub to the outer sleeve is configured to resist rotation between the cannula and the handle and maintain their relative positions until torque meeting a threshold condition is applied.

19. The endoscope of claim 13, in which the light source comprises at least four LEDs circumferentially arranged around an outer periphery of the video camera and recessed from a front face of a distal end of the cannula, said distal end of the camera having a rounded periphery facilitation insertion and movement of the cannula.

20. The endoscope of claim 13, in which the video screen is offset from a long axis of the cannula.

21. A hand-held endoscope comprising:
a single-use portion having a proximal housing, a mechanical connector integral with or affixed to the proximal housing, an electrical connector proximally spaced from the mechanical connector, a fluid hub that is rotatably mounted to the proximal housing and has a fluid port and is sealed against proximal fluid flow at a location distal from said mechanical connector, and a cannula extending distally from a distal portion of the fluid hub and having (i) a proximal port configured for fluid flow communication with the fluid hub's port, a distal fluid port, and a fluid lumen connecting the cannula's ports, and (ii) a video camera and a light source at a distal region;

a reusable portion comprising a handle, a video screen mounted thereon for rotation relative to the handle, a mechanical connector that is at a distal region of the handle is releasably mates and interlocks by hand with the single-use portion's mechanical connector and thus with the single-use portion, and an electrical connector that is proximally spaced from the reusable portion's mechanical connector and releasably mates by hand with the single-use portion's electrical connector to establish an electrical connection between the single-use and reusable portions;

wherein the fluid hub comprises a seal against fluid flow proximally from the fluid hub and into the proximal housing; and the single-use portion further comprises a splice-free cable extending from the video camera and light source to the single-use portion's electrical connector.

22. The endoscope of claim 21, in which the rotatable mount of the fluid hub to the proximal housing is configured to resist rotation and maintain the relative positions between the handle and cannula until the application of threshold torque exceeding 0.04 newton meters.

23. The endoscope of claim 21, in which the video screen is mounted for rotation between positions facing proximally and facing distally.

24. The endoscope of claim 21, in which the single-use portion's electrical connector extends proximally from the single-use portion's mechanical connector by a distance greater than a distance between the fluid hub and the handle, thereby facilitating protection of the electrical connectors of both the reusable portion and the single-use portion from fluid in the cannula and fluid hub.

25. The endoscope of claim 21, in which the handle's mechanical connector comprises a semicircular slot and distal projections surrounded by the slot, and the single-use portion's mechanical connector comprises a plate shaped and dimensioned to be snugly received in said semicircular slot and having flexible hooked tabs configured to engage the handle's tabs and secure the single-use and reusable portions to each other, and a pair of buttons connected to the flexible tabs and extending outside the circular plate, operative to press the flexible tabs by hand out of engagement with the handle's tabs to thereby allow the plate to slide out of the handle and thus permit removal of the single-use portion from the reusable portion.

26. The endoscope of claim 21 including a splice-free cable extending from the video camera and light source to the single-use portion's electrical connector.

27. An endoscopy method comprising:

providing a reusable portion with a mechanical connector at a distal region, an electrical connector at an intermediate region, and a video screen;

providing a single-use portion in sterile packaging that has an assembled set of (i) a cannula with a video camera, a light source, and a fluid port at a distal region, a fluid port at a proximal region, a fluid lumen between the fluid ports, and a cable lumen from the camera and light source to the distal region of the cannula, (ii) a fluid hub having a distal region secured to the proximal region of the cannula and a fluid port at an intermediate region in fluid flow communication with the port at the cannula's proximal region, (iii) a coupler that has a mechanical connector at an intermediate region, a distal region rotatably connected with a proximal region of the fluid hub, and an electrical connector at a region that extends proximally of the mechanical connector by at least the distance between the mechanical connector and the fluid hub;

unpacking the single-use portion and releasably (i) interlocking the mechanical connector of the coupler to the mechanical connector of the reusable portion by hand, and (ii) the electrical connector of the unpacked portion to the electrical connector of the reusable portion;

thereby releasably assembling an endoscope in which the electrical connection of the single-use to the reusable portion is separate and spaced proximally from the mechanical connection that interlocks the single-use and reusable portions to each other; and removing the single-use portion from the reusable portion by hand-action on a release mechanism formed by portions of the single-use portion and the reusable portion.

28. The method of claim 27, further configuring the rotatable connection between the coupler and the fluid hub to resist rotation until torqued to a threshold of at least 0.04 newton meters.

29. The method of claim 27, further including inserting a guide wire through the fluid hubs fluid port and into and through the cannula's fluid lumen and out of the cannula's distal fluid port.

30. The method of claim 27, further providing a splice-free electrical cable extending from the video camera and light source to the single-use portion's electrical connector.

31. The method of claim 27, further including rotating the video screen about an axis transverse to a long axis of the cannula between a proximal facing position and a distal facing position.

* * * * *